US012802784B2

(12) United States Patent
Schwartz et al.

(10) Patent No.: US 12,802,784 B2
(45) Date of Patent: Nov. 17, 2026

(54) HIGH THROUGHPUT MATERIALS SCREENING

(71) Applicant: Lawrence Livermore National Security, LLC, Livermore, CA (US)

(72) Inventors: Johanna Jesse Schwartz, Livermore, CA (US); Marissa Wood, Oakland, CA (US); Jianchao Ye, Tracy, CA (US); Adam Jaycox, Livermore, CA (US); Xiaoting Zhong, Livermore, CA (US); Aldair Gongora, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 451 days.

(21) Appl. No.: 18/468,563

(22) Filed: Sep. 15, 2023

(65) Prior Publication Data

US 2024/0096454 A1 Mar. 21, 2024

Related U.S. Application Data

(63) Continuation-in-part of application No. 17/932,723, filed on Sep. 16, 2022, now Pat. No. 12,474,238.

(51) Int. Cl.
*G16C 20/64* (2019.01)
*B29C 64/209* (2017.01)
(Continued)

(52) U.S. Cl.
CPC ............ *G16C 20/64* (2019.02); *B29C 64/209* (2017.08); *B29C 64/245* (2017.08); (Continued)

(58) Field of Classification Search
CPC ........ G16C 20/64; G16C 20/90; G16C 20/70; B29C 64/245; B29C 64/209; B29C 64/393; B33Y 30/00; B33Y 40/00; B33Y 50/02
(Continued)

(56) References Cited

U.S. PATENT DOCUMENTS 4,606,648 A * 8/1986 Coyle ...................... B01F 35/21
366/300
4,906,577 A * 3/1990 Armstrong ............. C12M 23/38
435/295.3
(Continued)

FOREIGN PATENT DOCUMENTS

EP 3747571 A1 * 12/2020 ........... B29C 64/393
EP 4007701 B1 * 10/2025 ................ B22F 1/10
(Continued)

OTHER PUBLICATIONS

Levi et al., In Situ Porous Structure Characterization of Electrodes for Energy Storage and Conversion by EQCM-D: a Review, Electrochimica Acta 232 (2017) 271-284 (Year: 2017).*
(Continued)

*Primary Examiner* — Stephanie E Bloss
*Assistant Examiner* — Kevin C Butler
(74) *Attorney, Agent, or Firm* — HARNESS, DICKEY & PIERCE PLC

(57) ABSTRACT

The present disclosure relates to systems and methods for screening a formulation of a material being printed in an additive manufacturing process, in situ, to enable rapid analysis, modeling and modification of at least one characteristic associated with the material formulation. In one embodiment the system includes a computer and an experimental planning software module that includes a historical database of sample material test results, a machine learning software module, and a new batch formulation generation software module. The experimental planning software module enables new material formulations to be determined in situ and in real time, using one or more machine learning models, and new material samples to be printed in accordance with newly determined material formulations, for
(Continued)

closer inspection and evaluation of at least one desired characteristic of the sample materials.

19 Claims, 11 Drawing Sheets

(51) Int. Cl.

| | |
|---|---|
| ***B29C 64/245*** | (2017.01) |
| ***B29C 64/393*** | (2017.01) |
| ***B33Y 30/00*** | (2015.01) |
| ***B33Y 40/00*** | (2020.01) |
| ***B33Y 50/02*** | (2015.01) |
| ***G16C 20/70*** | (2019.01) |
| ***G16C 20/90*** | (2019.01) |

(52) U.S. Cl.
CPC ............ *B29C 64/393* (2017.08); *G16C 20/70* (2019.02); *G16C 20/90* (2019.02); *B33Y 30/00* (2014.12); *B33Y 40/00* (2014.12); *B33Y 50/02* (2014.12)

(58) Field of Classification Search
USPC .......................................... 427/421; 73/150 R
See application file for complete search history.

(56) References Cited

U.S. PATENT DOCUMENTS

| | | | | |
|---|---|---|---|---|
| 10,071,350 | B2 * | 9/2018 | Lewis | B28C 5/1292 |
| 10,375,765 | B2 * | 8/2019 | Chaffins | H05K 1/16 |
| 10,406,801 | B2 * | 9/2019 | Bell | B33Y 10/00 |
| 10,518,480 | B2 * | 12/2019 | Putman | G06V 20/64 |
| 10,710,301 | B2 * | 7/2020 | Feng | B33Y 30/00 |
| 10,717,232 | B2 * | 7/2020 | Feng | B33Y 10/00 |
| 10,857,778 | B2 * | 12/2020 | Mantha | B29C 64/106 |
| 10,926,464 | B2 * | 2/2021 | Chaffins | B33Y 80/00 |
| 10,967,559 | B2 * | 4/2021 | Huang | B33Y 80/00 |
| 11,090,862 | B2 * | 8/2021 | Chaffins | H05K 1/095 |
| 11,123,895 | B2 * | 9/2021 | Heng | B28B 1/001 |
| 11,123,930 | B2 * | 9/2021 | Bheda | B33Y 50/02 |
| 11,239,422 | B2 * | 2/2022 | McAlpine | H10K 50/115 |
| 11,559,607 | B2 * | 1/2023 | Kolesky | A01N 1/16 |
| 11,858,039 | B2 * | 1/2024 | Sajadi | B33Y 80/00 |
| 11,867,644 | B2 * | 1/2024 | Ros | B33Y 80/00 |
| 11,910,931 | B2 * | 2/2024 | Achten | B33Y 30/00 |
| 11,911,825 | B2 * | 2/2024 | Erickson | B29C 70/882 |
| 12,037,603 | B2 * | 7/2024 | Retting | C12N 5/0656 |
| 12,115,697 | B2 * | 10/2024 | Heng | B29C 64/209 |
| 12,291,603 | B2 * | 5/2025 | Kuno | B33Y 10/00 |
| 2003/0085267 | A1 * | 5/2003 | Piotrowski | G06Q 30/02 235/375 |
| 2003/0230138 | A1 * | 12/2003 | Bast | C23C 16/52 73/150 R |
| 2016/0346997 | A1 * | 12/2016 | Lewis | B33Y 80/00 |
| 2017/0326867 | A1 * | 11/2017 | Hartke | B29C 64/153 |
| 2018/0071868 | A1 * | 3/2018 | Goehler | B29C 64/153 |
| 2018/0133670 | A1 * | 5/2018 | Lewis | B01F 23/53 |
| 2018/0159037 | A1 * | 6/2018 | McAlpine | H10K 50/115 |
| 2019/0329322 | A1 * | 10/2019 | Preston | H04N 1/00037 |
| 2020/0101670 | A1 * | 4/2020 | Howell | G06V 10/82 |
| 2020/0223146 | A1 * | 7/2020 | Totzeck | G01N 29/043 |
| 2020/0298492 | A1 * | 9/2020 | Yirmibesoglu | B29B 7/826 |
| 2020/0384693 | A1 * | 12/2020 | Bennett | B29C 64/153 |
| 2021/0197279 | A1 * | 7/2021 | Sohn | B23K 26/144 |
| 2021/0260829 | A1 * | 8/2021 | Hosseini Rankouhi | B22F 10/38 |
| 2022/0266522 | A1 * | 8/2022 | Jackson | B22F 12/43 |
| 2025/0205969 | A1 * | 6/2025 | Almubarak | B29C 64/241 |
| 2025/0221824 | A1 * | 7/2025 | Dikovsky | B29C 64/112 |
| 2025/0262810 | A1 * | 8/2025 | Ng | B29C 48/05 |
| 2025/0361414 | A1 * | 11/2025 | Bukovsky | B29C 64/106 |

FOREIGN PATENT DOCUMENTS

| | | | | | |
|---|---|---|---|---|---|
| KR | 102226094 | B1 * | 3/2021 | G01N 21/1702 |
| WO | WO-2014209994 | A2 * | 12/2014 | B29C 64/118 |
| WO | WO-2015069619 | A1 * | 5/2015 | A61L 27/3826 |
| WO | WO-2015073944 | A2 * | 5/2015 | G01L 1/2287 |
| WO | WO-2015120429 | A1 * | 8/2015 | B33Y 80/00 |
| WO | WO-2016082810 | A1 * | 6/2016 | G06F 30/20 |
| WO | WO-2016164562 | A1 * | 10/2016 | B41J 2/175 |
| WO | WO-2018091091 | A1 * | 5/2018 | H04L 67/104 |
| WO | WO-2018234331 | A1 * | 12/2018 | G06F 30/20 |
| WO | WO-2025217022 | A1 * | 10/2025 | B33Y 10/00 |

OTHER PUBLICATIONS

Krueger et al., Solid Electrolyte Interphase Evolution on Lithium Metal Electrodes Followed by Scanning Electrochemical Microscopy Under Realistic Battery Cycling Current Densities, ChemElectroChem, ChemElectroChem 2020, 7, 3590-3596 (Year: 2020).*

Silau et al., Weibull Analysis of Electrical Breakdown Strength as an Effective Means of Evaluating Elastomer Thin Film Quality, Advanced Engineering Materials, 20(9), Article 1800241. https://doi.org/10.1002/adem.201800241, (2018), 23 pg(s) (Year: 2018).*

Taylor et al., An insight into the errors and uncertainty of the lithium-ion battery characterisation experiments, Elsevier., 2019, 24 pg(s) (Year: 2019).*

Tashman et al., A high performance open-source syringe extruder optimized for extrusion and retraction during Fresh 3D bioprinting, HardwareX 9 (2021) e00170 (Year: 2021).*

Darling et al., Syringe pump extruder and curing system for 3D printing of photopolymers, HardwareX 9 (2021) e00175 (Year: 2021).*

Roland Yingjie Tay et al., Direct-ink-writing 3D-printed bioelectronics, aterials Today d vol. xxx, No. xx d xxxx, https://doi.org/10.1016/j.mattod.2023.09.006, 2023 (Year: 2023).*

Peishi Yu et al., Sensor Array with Optimized Circuit Layout, Chinese Journal of Mechanical Engineering (2023) 36:88, https://doi.org/10.1186/s10033-023-00916-3 (Year: 2023).*

Saadi et al., Direct Ink Writing: A 3D Printing Technology for Diverse Materials, Advanced Materials, 2022, 34 (Year: 2022).*

Krueger et al., Solid Electrolyte Interphase Evolution on Lithium Metal Electrodes Followed by Scanning Electrochemical Microscopy Under Realistic Battery Cycling Current Densities, ChemElectroChem, 2020, 7, 3590-3596 (Year: 2020).

ISA International Search Report and Written Opinion in corresponding International Patent Application PCT/US2023/032932 mailed Feb. 5, 2024, 8 pp.

* cited by examiner

HIGH THROUGHPUT MATERIALS SCREENING

CROSS-REFERENCE TO RELATED APPLICATIONS

This application is a Continuation-in-part Applications and claims priority of U.S. patent application Ser. No. 17/932,723 filed on Sep. 16, 2023. The entire disclosure of the above application is incorporated herein by reference.

STATEMENT AS TO RIGHTS TO APPLICATIONS MADE UNDER FEDERALLY SPONSORED RESEARCH AND DEVELOPMENT

This invention was made with Government support under Contract No. DE-AC52-07NA27344 awarded by the United States Department of Energy. The Government has certain rights in the invention.

BACKGROUND

Field of Endeavor

The present application relates to materials screening and more particularly to high throughput materials screening.

State of Technology

This section provides background information related to the present disclosure which is not necessarily prior art.

Polymer materials formulation and optimization has been generally limited to mixing by hand, as polymers have a wide range of viscosities. A high throughput approach is therefore needed to enable faster screening of polymers optimized for targeted applications. Systems that mix multi-materials with disparate viscosities are known [Example U.S. Pat. No. 10,071,350]. The inventors have developed active mixing direct-ink-write (DIW) additive manufacturing to facilitate the 3D printing of multi-material films. The inventors have developed an automated platform for materials by coupling mixing systems with in-situ characterization systems combined with machine learning systems.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Applicant's apparatus, systems, and methods provide screening for screening a material that includes providing active mixing direct-ink-writing of the material, providing in situ characterization substrates or probes that receive the material, and providing active learning planning for screening the material. The providing active mixing direct-ink-writing of the material prints multiple films. In one embodiment the providing active mixing direct-ink-writing of the material prints five to ten films. In another embodiment the providing active mixing direct-ink-writing of the material prints one to twenty films. The providing in situ characterization substrates or probes includes printing multiple films on the substrates or probes with a first set of constituents. The providing active learning planning for screening the material includes providing machine learning that takes the first set of constituents and uses the first set of constituents to dictate a next batch of films to achieve improved additional sets of constituents.

In one aspect the Applicant's system relates to a system for screening a formulation of a material being printed in an additive manufacturing process, in situ, to enable rapid analysis, modeling and modification of at least one characteristic associated with the material formulation. The system may comprise a computer. A substrate may be included on which the material formulation is printed. A deposition print head may be included for depositing the material formulation on the substrate as at least one material sample. The substrate may include at least one component for enabling the characteristic of the material formulation printed thereon to be at least one of measured or determined. A probe is included which is configured to be moved into contact with the material formulation after the material formulation is printed on the substrate as a sample material. The probe provides an output to the computer representing data from which the characteristic can be evaluated by the computer and a new material formulation determined. An experimental planning software module may be included which has a machine learning software module. The machine learning software module is configured to use the data collected by the probe and to determine, using the machine learning software module, a new material formulation which better optimizes the characteristic being evaluated.

In another aspect the deposition print head of the system includes at least first and second input ports for receiving first and second components of the material formulation being supplied to the deposition print head.

In another aspect the system further comprises at least first and second syringes for containing the first and second components, respectively, of the material formulation, and which first and second motors associated with the first and second syringes, respectively. The first and second motors are responsive to control signals from the computer for controllably providing the first and second components to the deposition print head in accordance with the control signals from the computer.

In another aspect the computer generates the control signals in real time, and in situ, at least one of while or before the material sample is being printed.

In another aspect the experimental planning software module further includes a database for storing information and/or data associated with previously screened test materials. The database is configured to be updated in real time with new material screening results provided by the probe output and updated formulation suggestions by the machine learning software module. A new batch formulation software module is also included for receiving information from the database and generating new formulations for a new batch of material samples to be printed.

In another aspect the machine learning software module comprises at least one of a random forest model, a gaussian process model or a neutral network model.

In another aspect the machine learning module comprises a Bayesian optimization framework for carrying out Bayesian modeling and decision making.

In another aspect, the at least one component of the substrate comprises a grid of spatially separated electrodes which are used to complete electrical paths as the probe contacts different areas of the material sample after the material sample is printed on the substrate, to thus enable the probe to generate the output to the computer.

In another aspect the probe comprises a two point probe head including a first component which makes contact with the material sample, and a second component which extends through the material sample and into contact with at least one of the electrodes.

In another aspect the at least one component of the substrate comprises an environmental sensor.

In another aspect the at least one component of the substrate comprises stress sensors.

In another aspect the at least one component of the substrate comprises an impedance sensor.

In another aspect the at least one component of the substrate comprises at least one of an O2 sensor, a thermal sensor or a pH sensor.

In another aspect cells are included in the material formulation when the material sample is printed on the substrate by the deposition print head. The cells provide information enabling the characteristic to be evaluated.

In another aspect a microscopy or fluorescence imaging subsystem is included for assisting in evaluating the material sample.

In another aspect the build plate comprises at least one of an embedded gas or a chemical sensor for generating information to assist the computer in evaluating the material sample printed on the build plate.

In another aspect substrate and deposition print head are located inside a controlled environment.

In another aspect the controlled environment includes a stimulus to assist in evaluation of the material sample.

In another aspect a secondary environmental chamber is included which communicates with the controlled environment to enable further study of a component present in the controlled environment.

In another aspect the present disclosure relates to a method for screening a formulation of a material being printed in an additive manufacturing process, in situ, to enable rapid analysis, modeling and modification of at least one characteristic associated with the material formulation. The method may comprise printing the material formulation as at least one material sample on a substrate, and then using at least one component associated with the substrate for enabling the characteristic of the material formulation printed thereon to be at least one of measured or determined. The method may further include using a probe to obtain information concerning the characteristic from the material sample. The method may include causing the probe to provide an output to a computer, and then causing the computer to use software to evaluate the material sample. The software includes machine learning software to evaluate historical data concerning previously printed material samples, and to assist in determining updated formulations for new material samples to be printed on the substrate in subsequent printing operations and further analyzed.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1A:
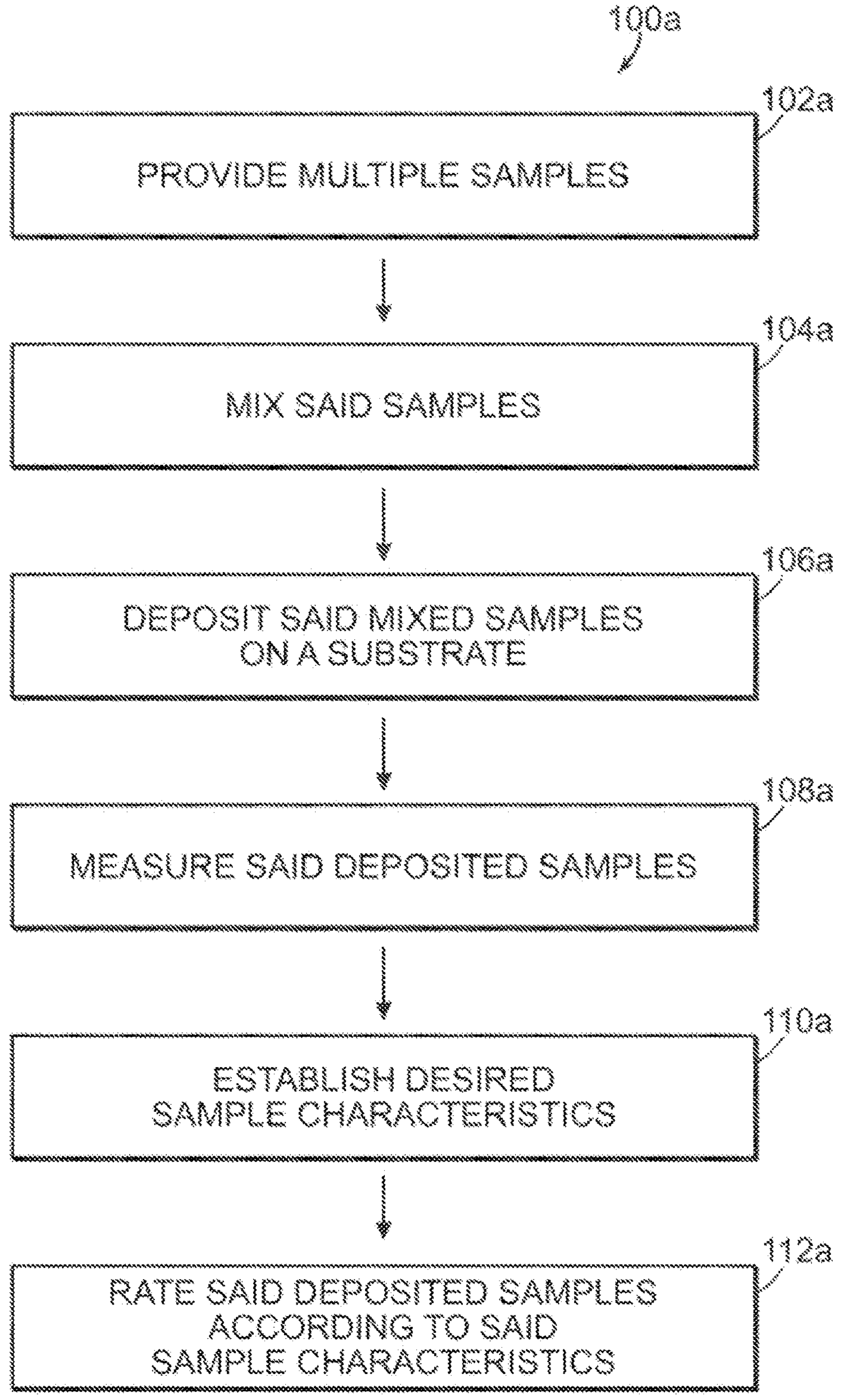
FIG. 1A is a flowchart that illustrates one embodiment of a screening method for screening a material.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Applicant's apparatus, systems, and methods provide active-mixing direct ink write additive manufacturing enable mixing of materials with highly disparate viscosities, from liquids to pastes. By coupling a mixing system with in-situ characterization methods, and also with machine learning experimental planning systems, the inventors have developed an automated platform for materials discovery and optimization. The systems and methods of the present disclosure can handle complex hybrid formulations including, but not limited to, solvents, monomers, oligomers, polymers, and additives. Additives can be liquid or solid, including particles (nano and micro) of organic compounds, metals, salts, glasses, ceramics, conducting materials, and more. In-situ characterization using a suitable component, for example either through a probe or substrate matrix, enables information to be obtained to facilitate homing-in on desirable properties for target applications when coupled with use of an active learning experimental planning software to vary the composition during the printing process.

Referring now to the drawings and in particular to FIG. 1A, an illustrative view shows an embodiment of Applicant's apparatus, systems, and methods. This embodiment is identified generally by the reference numeral 100*a*. FIG. 1A is a flowchart that illustrates a screening method for screening a material. The component steps of Applicant's method 100*a* illustrated in FIG. 1A are listed below:

- Reference Numeral No. 102*a*—provide multiple selected samples,
- Reference Numeral No. 104*a*—mix the samples,
- Reference Numeral No. 106*a*—deposit the mixed samples on a substrate,
- Reference Numeral No. 108*a*—measure the deposited samples,
- Reference Numeral No. 110*a*—establish desired sample characteristics, and
- Reference Numeral No. 112*a*—rate the deposited samples according to the sample characteristics.

The description of the steps of the Applicant's material screening method 100*a* having been completed, the operation and additional description of the Applicant's apparatus, systems, and methods will now be considered in greater detail.

The screening method 100*a* includes the steps of providing active mixing direct-ink-writing of the material, providing in situ characterization components such, for example substrates or probes, containing the material, and providing active learning planning for screening the material. The step of providing active mixing direct-ink-writing of the material may involve printing a select number of films, for example printing five to ten films. The step of providing in situ characterization substrates or probes includes printing multiple films on the substrates or probes with the multiple films having a first set of constituents. For example, the step of providing in situ characterization substrates or probes can include printing five to ten films on the substrates or probes with the five to ten films having a first set of constituents. In another example, the step of providing in situ characterization substrates or probes includes printing one to twenty films on the substrates or probes with the one to twenty films having a first set of constituents.

The step of providing active learning planning for screening the material includes providing machine learning that takes the first set of constituents and uses the first set of constituents to dictate a next batch of films to achieve improved additional sets of constituents. As illustrated in FIG. 1A, step 102*a* involves providing multiple samples. Step 104*a* involves mixing the samples. Step 106*a* involves depositing the mixed samples on a substrate. Step 108*a* involves measuring the deposited samples. Step 110*a* involves establishing desired sample characteristics. Step 112*a* involves rating the deposited samples according to said sample characteristics.

Figure 1B:
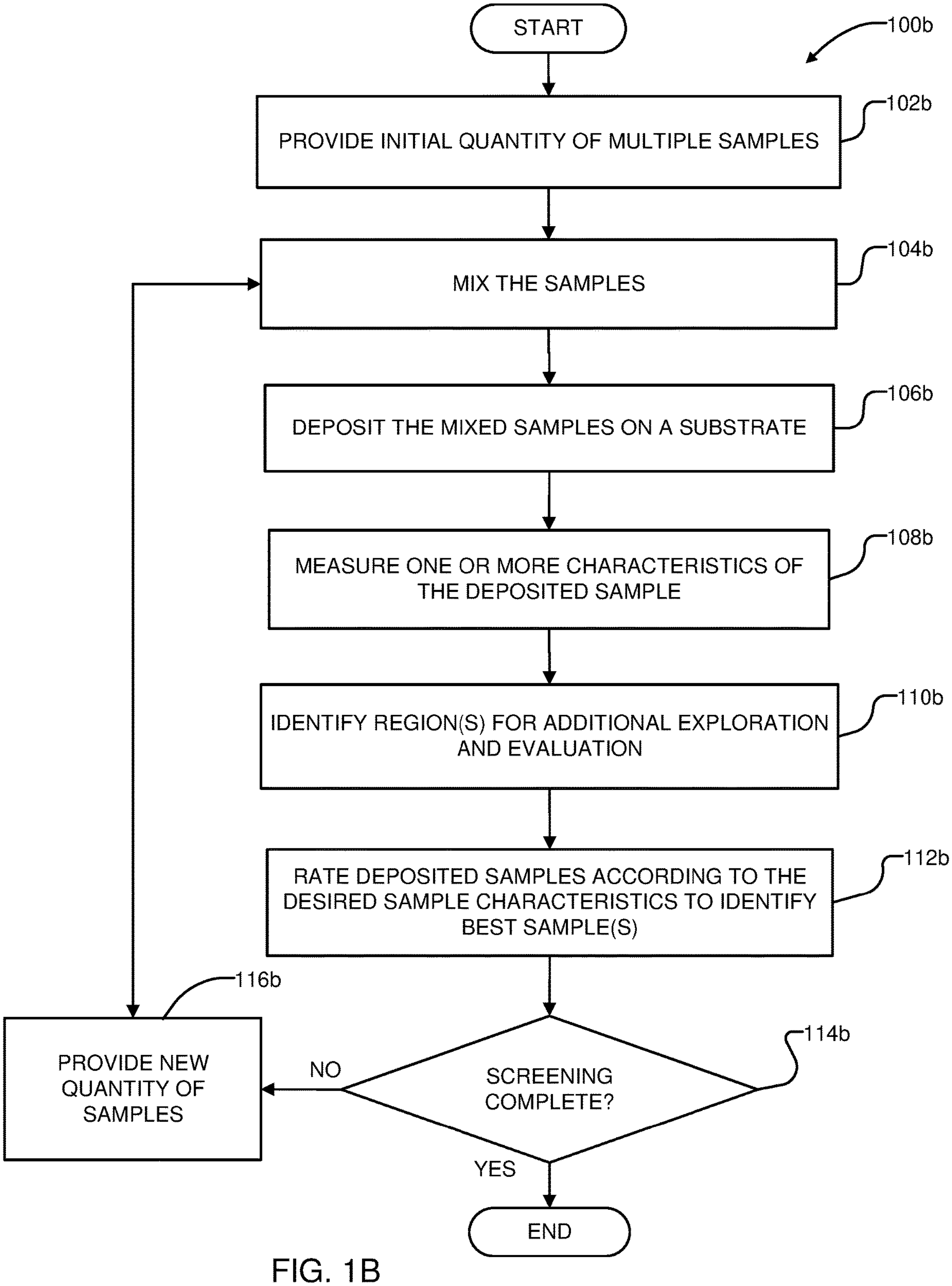
FIG. 1B is a flowchart that illustrates another embodiment of a screening method for screening a material.

Referring now to FIG. 1B, an illustrative view shows another embodiment of Applicant's apparatus, systems, and methods. This embodiment is identified generally by the reference numeral 100*b*. FIG. 1B is a flowchart that illustrates a screening method for screening a material. The component steps of Applicant's method 100*b* illustrated in FIG. 1*b* are listed below:

- Reference Numeral No. 102*b*—provide multiple samples,
- Reference Numeral No. 104*b*—mix said samples,
- Reference Numeral No. 106*b*—deposit said mixed samples on a substrate,
- Reference Numeral No. 108*b*—measure said deposited samples,
- Reference Numeral No. 110*a*—establish desired sample characteristics,
- Reference Numeral No. 112*b*—rate said deposited samples according to said sample characteristics,
- Reference Numeral No. 114*b*—screening complete check, and
- Reference Numeral No. 116*b*—provide new quantity of samples for further testing.

The description of the steps of the Applicant's material screening method 100*b* having been completed, the operation and additional description of the Applicant's apparatus, systems, and methods will now be considered in greater detail.

The screening method 100*b* includes the steps of providing active mixing direct-ink-writing of the material, providing in situ characterization substrates or probes containing the material, and providing active learning planning for screening the material. The step of providing active mixing direct-ink-writing of the material prints five to ten films. The step of providing in situ characterization substrates or probes includes printing multiple films on the substrates or probes with the multiple films having a first set of constituents. For example, the step of providing in situ characterization substrates or probes can include printing five to ten films on the substrates or probes with the five to ten films having a first set of constituents. In another example, the step of providing in situ characterization substrates or probes includes printing one to twenty films on the substrates or probes with the one to twenty films having a first set of constituents.

The step of providing active learning planning for screening the material includes providing machine learning that takes the first set of constituents and uses the first set of constituents to dictate a next batch of films to achieve improved additional sets of constituents. As illustrated in FIG. 1B step 102*b* provides multiple samples. Step 104*b* mixes the samples. Step 106*b* deposits the mixed samples on a substrate. Step 108*b* measures select characteristics or qualities of the deposited samples. Step 110*b* identifies one or more regions of the deposited samples for additional exploration, which may involve exploring unknown spaces between the deposited samples. Step 112*b* rates the deposited samples according to said sample characteristics. By "rates" it is meant evaluates the best sample(s) of interest according some at least one predetermined parameter (e.g., ionic conductivity). Step 114*b* involves making a check to determine if screening is complete. By "complete" it is meant that no additional space is available on the substrate or that a predetermined number of samples have been deposited. If this check produces a "NO" answer, then a new quantity of samples is provided at operation 116*b*, and steps 104*b*-114*b* are repeated. If the check at operation 114*b* produces a "YES" answer, then screening is completed.

Figure 2:
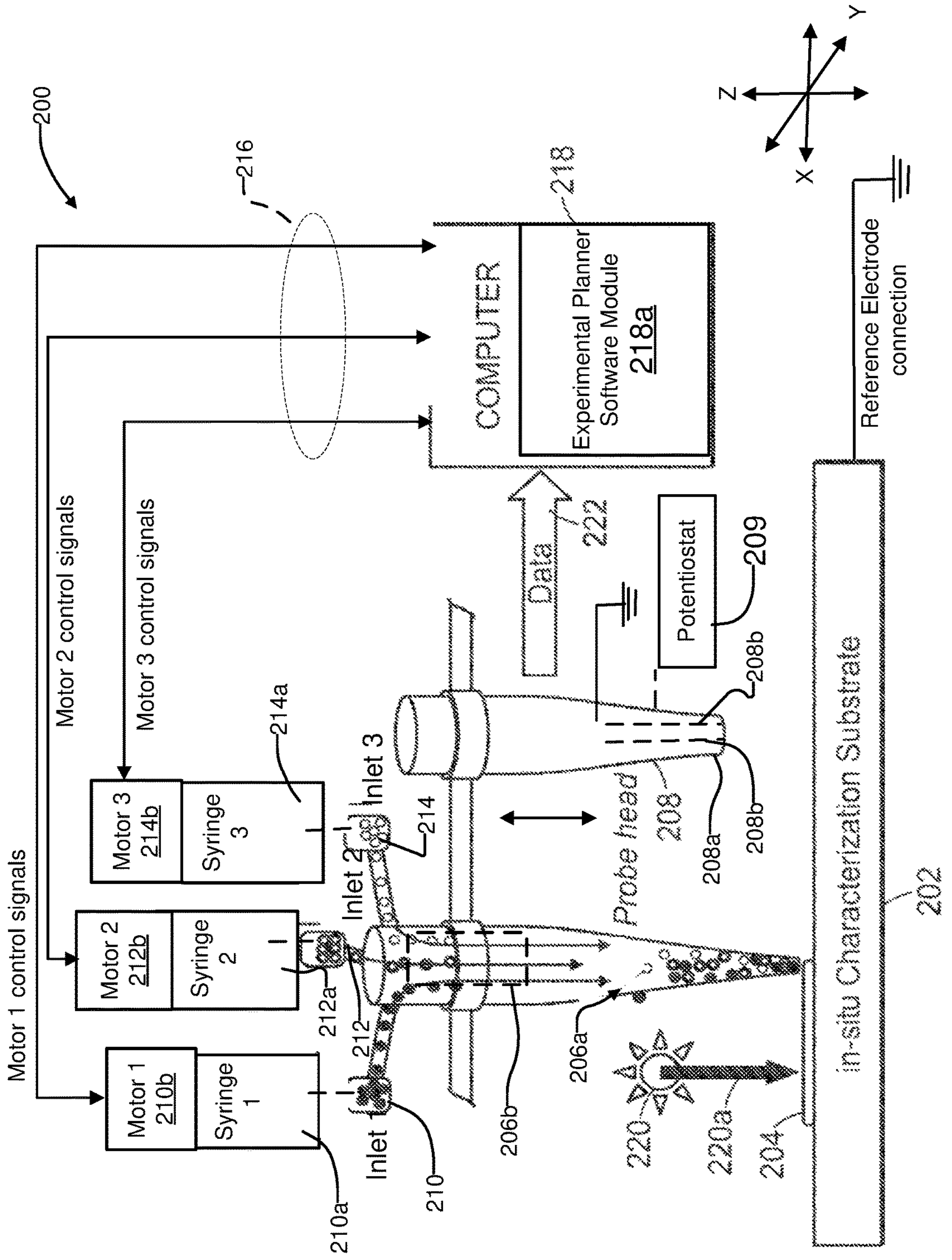
FIG. 2 is an illustration of Applicant's apparatus, systems, and methods that involve three main components: Formulations loading and mixing, Deposition and measurement, and Analysis and experimental planning.

Referring now to FIG. 2, an illustrative view shows another embodiment of Applicant's apparatus, systems, and methods. This embodiment is identified generally by the reference numeral 200. The components of Applicant's apparatus, systems, and methods 200 illustrated in FIG. 2 are listed below:

Reference Numeral No. 202—In-situ Characterization Substrate,
Reference Numeral No. 204—Deposited Formulation,
Reference Numeral No. 206—Mixing and Deposition Head or Nozzle,
Reference Numeral No. 206*a*—Rotationally Driven Mixing Shaft Element,
Reference Numeral No. 208—Probe Head,
Reference Numeral No. 208*a*—Probe Tip,
Reference Numeral No. 208*b*—Probe Push Pins,
Reference Numeral No. 210—Inlet 1,
Reference Numeral No. 210*a*—Syringe 1,
Reference Numeral No. 210*b*—Motor 1,
Reference Numeral No. 212—Inlet 2,
Reference Numeral No. 212*a*—Syringe 2,
Reference Numeral No. 212*b*—Motor 2,
Reference Numeral No. 214—Inlet 3,
Reference Numeral No. 214*a*—Syringe 3,
Reference Numeral No. 214*b*—Motor 3,
Reference Numeral No. 216—Signal bus,
Reference Numeral No. 218—Computer,
Reference Numeral No. 218*a*—Experimental Planner Software Module for Analyzing Probe Data and Generating New Sample Formulation(s),
Reference Numeral No. 220—Photocuring light source,
Reference Numeral No. 220*a*—Photocuring light, and
Reference Numeral No. 222—Data from Probe Head.

The description of the structural components of the Applicant's apparatus, systems, and methods 200 having been completed, the operation and additional description of the Applicant's apparatus, systems, and methods will now be considered in greater detail. Applicant's apparatus, systems, and methods 200 involve three main components or operations: (1) Formulations loading and mixing, (2) Deposition and measurement, and (3) Analysis and experimental planning.

General Description of Operation of FIG. 2

Load test samples from syringes 210*a*, 212*a* and 214*a* into inlets 210, 212, and 214, respectively via control signals provided by the computer 218 to each of motors 210*b*, 212*b* and 214*b*, which force the test samples at desired flow rates out from their respective syringes and into the inlets 1, 2 and 3.

Use the deposition head 206 to mix and deposit 204 films in batches on the substrate 202.

Cure materials onto substrate 202 using photocuring light 220*a*.

Measure impedance through contact between the probe 208 and In-situ Characterization Substrate 202.

Record data of batch of just-deposited test samples on the computer 218.

Automated software 218*a* takes data from previous batches and analyzes the data relative to the data associated with the just-deposited samples, to determine samples to be used for the next batch printed 216.

Repeat until done (i.e., when substrate is filled or no more space is available for sample deposition onto the substrate 202—Applicant contemplates up to 100 samples in a single screening).

More Detailed Description of Operation of FIG. 2

Prior to deposition, sample materials of interest are first loaded into the inlets 210, 212, and 214 via suitable control signals applied to the motors 210*b*, 212*b* and 214*b* associated with the syringes 210*a*, 212*a* and 214*a*, respectively. It will be appreciated that this is but one suitable means for supplying the sample materials of interest to the Inlets 210, 212 and 214 of the print head 206. Any means of controlling the sample material flow into the inlets 210, 212 and 214 through electrical control signals from the computer 218 may be used to supply the sample material. The control signals applied to each motor 210*b*, 212*b* and 214*b* from the computer 206 via signal bus 216 control the flow rate of material out from the syringes 210*a*, 212*a* and 214*a*, respectively, so the quantity of each sample material can be closely controlled. Note that FIG. 2 shows the deposition nozzle 206 having three inlets; however, more inlets are contemplated and only three are shown for illustrative purposes. In some instances two inlets, or possibly even only one inlet, may be provided.

Each of the inlets 210, 212 and 214 of the deposition head 206 receives one of the sample materials of interest. Examples of the samples include polymer electrolyte resin formulations including components such as solvents, monomers, oligomers, polymers, initiators and curing agents, salts, stabilizers, plasticizers, and solid additives such as silica, ceramics, nanoparticles, and metals. Once the inlets 210, 212, 214 are loaded, this provides the sample formulation 204 which will be mixed within the deposition nozzle 206. The ratios of sample materials supplied to the inlets 210, 212 and 214 can be kept constant or varied throughout testing by suitable control signals from the computer 218, which serve to controllably vary the flow of the sample materials out from each of the syringes 210*a*, 210*b* and 210*c*, thus producing deposited materials with homogeneous, heterogenous, and/or graded compositions. Mixing of the sample materials within the deposition nozzle 206 can be achieved through static or active mixing techniques. Active mixing techniques are illustrated in FIG. 2 and utilize a rotating mixing shaft element 206*b* within the deposition head 206 to shear mix the inlet materials. Active mixing is generally chosen for polymer electrolytes, as homogenous mixing of formulations with viscosities ranging from liquids to gels and pastes is possible. The rotational rate of the mixing shaft 206*b*, coupled with the feed rate of the sample materials being supplied to the inlets 210, 212 and 214, impacts the mixing time and turbidity within the system 200, and thereby the homogeneity of each mixed sample formulation 204 which is deposited onto the substrate 202. The deposition nozzle 206 may include shear, pressure, and thermal inputs to enable deposition and analysis of the mixed sample formulations 204. In one embodiment the mixing shaft may be controlled by the computer 218 or possibly by a separate controller associated with the deposition nozzle 206 (i.e., the printer system associated with the deposition nozzle).

Mixed sample formulations 204 are then deposited onto the substrate 202. Deposited samples formulations 204 can include liquids, gels pastes, and thermoplastics. With the inclusion of crosslinkers, the mixed sample formulations 204 can be cured using photo, thermal, chemical, or other curing mechanisms. In the case of polymer electrolyte formulations, traditional photocuring methods are used through the inclusion of light generated by photocuring light source 220 during printing. Curing enables the deposition of multiple stacked layers, and the system 200 can handle thin film and three-dimensional structures depending on the application. For screening, thin films are generally targeted. In the case of system 200, polymer electrolyte measurements are focused on impedance characterization. With contact between the two point probe 208 and the electrode connections on the substrate 202, electrical impedance spectroscopy measurements are made traditionally from frequencies of 7 MHz to 100 mHz. Ranges of 35 MHz to 10 μHz are possible. Over twelve measurements are possible for a single film, moving the probe head 208 spatially around on the thin film to position it at various points over the spatially varied electrode connections. Traditionally, 4-6 spatial measurements are done for each deposited thin film. Measurements are done in triplicate, and the average of all measurements for one film is used and recorded in the database for the sample for comparison. Additional probe heads and substrates contemplated for use in the system 200 include optical metrology and imaging, stress sensing, chemical compositional analysis, fluorescence, pH, and environmental measurements (temperature, humidity). In addition, probe head 208 and substrate 202 can be utilized to align and interact with deposited materials. This includes electromagnetic alignment of particles, electrochemical and surface chemistry interactions, and photo or thermal curing and interactions. Probe head 208 and substrate 202 inputs and measurement 220 information are controlled and recorded as data within the computer 218 and its respective experimental planner software module 218*a*. This data is kept for each print and formulation tested.

With specific regard to the probe head 208, in one embodiment the probe head 208 forms a "two-point" impedance probe head and includes a probe tip 208*a* which when lowered that makes contact with the surface of the just-printed sample, and a pair of push pins 208*b* that can be lowered further to extend through the sample and make contact with a selection of two electrodes of the substrate 202, and thus complete an electrical path for an impedance measurement across the polymer electrolyte. In another embodiment the substrate 202 itself may include connections between the electrodes of the substrate and ground, which eliminates the need for the two-point feature of the probe head 208, allowing the probe to make contact only with the sample for impedance measurement. In another embodiment the substrate 202 itself may include connections between the electrodes of the substrate, the potentiostat, and ground, which eliminates the need for a probe head altogether. In still another embodiment three or more push pins 208*b* may be included in the probe to assist in making impedance spectroscopy measurements.

Figure 2A:
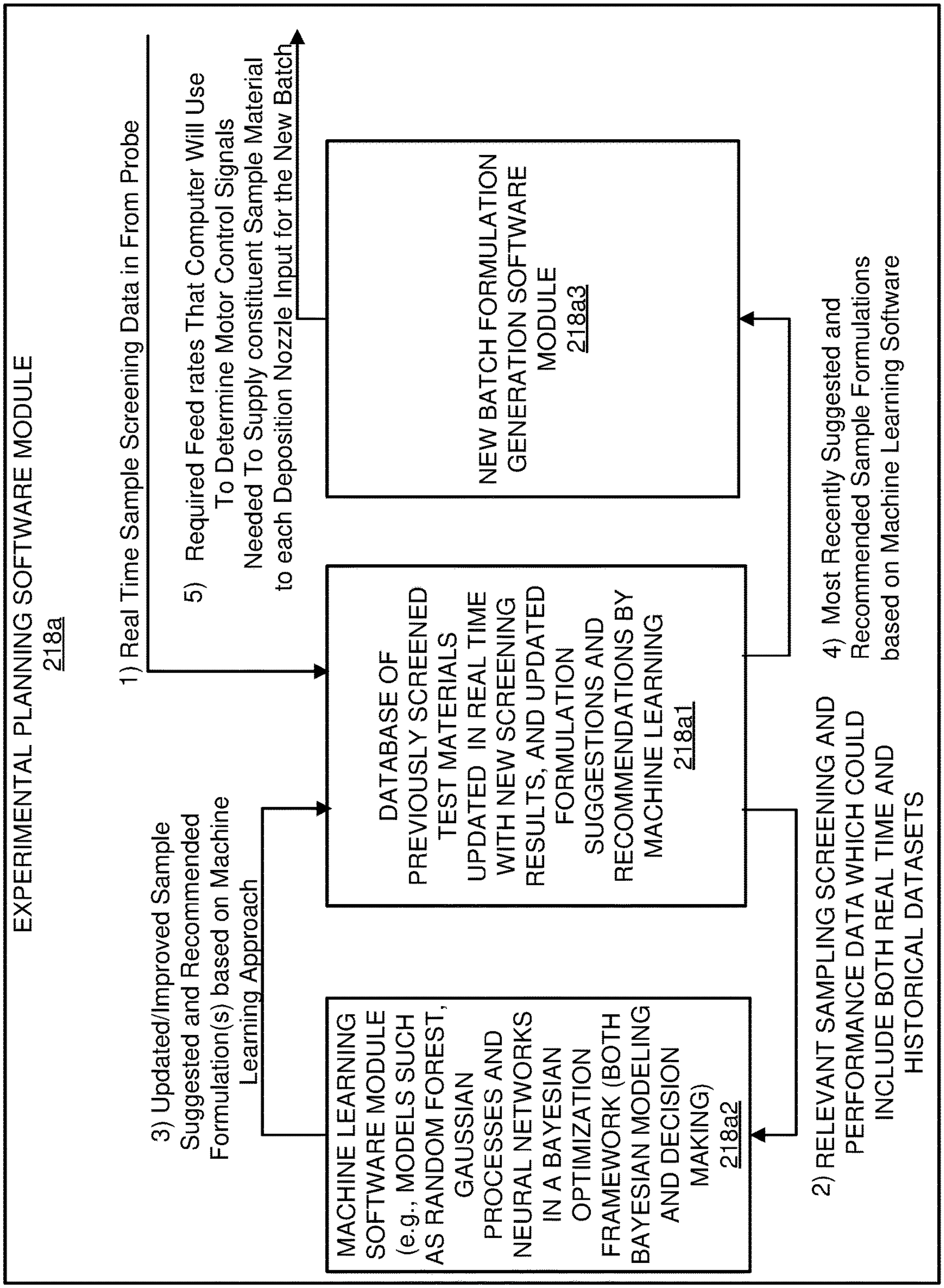
FIG. 2A is a high level block diagram illustrating in more detail the various components of the experimental planning software module.

Referring briefly to FIG. 2A, a high level block diagram can be seen of the experimental planner software module 218*a* that the system 200 includes. In this example the experimental planner software module 218*a* includes a database 218*a*1, a machine learning software submodule 218*a*2, and a new batch formulation generation software submodule 218*a*3. The database 218*a*1 receives and is updated with newly obtained screening results from the probe 208 in real time. The database 218*a*1 also receives updated/improved sample formulation(s) which are calculated by a machine learning software module 218*a*2. The new batch formulation generation software submodule 218*a*3 uses the most recently calculated batch formation(s) information generated by the machine learning software submodule 218*a*2 and generates the new material flow rates needed to apply to each constituent material in the syringes 210*a*, 212*a* and 214*a*, for the new sample material batch. The newly calculated feed rates are used by the computer 218 to generate the needed motor control signals to control the inlet 210, 212 and 214 sample material feed ratios during screening. Between tests, the machine learning models contained in the machine learning software submodule 218*a*2 are improved through repeated and strategic analysis of the full living database 218*a*1 of previous test materials screened. Machine learning models that may be included in the machine learning software submodule 218*a*2 may include, but are not limited to, for example, Bayesian optimization algorithms that use models such as Random Forest and Gaussian Processes, as well as large data models including Neural Networks. During sample deposition and testing, the latest model is used to analyze the data from previous batches of testing. From this data, a new batch of formulations is generated by the experimental planning software module 218*a* for the next test or tests, which may include, but are not limited, for example, Bayesian optimization algorithms that use decision policies such as upper confidence bound (UCB), and printing continues. This new batch data is will again be analyzed by the experimental planning software module 218*a* against the next obtained sample data received from the probe 208, and again used to create still another new batch formulation. In other words, all data generated during a test, both historical and real time data, are used to make the new batch of testing, until testing is completed. Then this data is once again added to the database 218*a*1 and used to improve the calculated formulations generated by the experimental planning software module 218*a*. Critically, the experimental planning software module 218*a* enables full automation of the materials formulation screening, enabling rapid homing in on desirable properties (i.e., ionic conductivity) from the characterization and measurement data obtained by the probe 208 during testing.

Example of Polymer Electrolyte Printing

1) Material formulations are made using any combination, without limitation, of the following components: solvent, monomer, oligomer, polymer, crosslinkers, salts, photoinitiators, catalysts, stabilizers, dyes, liquid additives and solid additives. Viscosities from liquids to high viscosity gels and pastes are possible.

2) Components making up formulations are loaded into the inlet syringes 210*a*, 212*a*, 214*a* and motor ratios are used to control the varying composition. Two to four different syringe inlets are possible, with traditional testing using two syringes to vary a single variable. Example variables include, without limitation, salt concentration, additive concentration, and polymer additive concentration.

3) Components from each syringe 210*a*, 212*a* and 212*b* are mixed in the deposition nozzle 206 and deposited onto the characterization substrate 202. The rotational speed of each of the motors 210*b*, 212*b* and 214*b*, and pressures created therefrom in each syringe 210*a*, 212*a* and 214*a*, dictate turbidity, deposition rate, and homogeneity of the formulations fed into the deposition nozzle 206. Samples are generally printed at a fixed motor feed ratio (fixed composition), but compositions may be switched between samples in a given test. For sample quantity, depending on the dimensions of the characterization substrate 202, anywhere from 1-100 samples are possible in a single print run. Samples may also be graded or heterogeneous, with ratios between components of the formulation being switched or modified mid-print. A dump region on the characterization substrate 202 is used to switch between different compositions between samples.

4) UV or blue light is traditionally used to cure the samples during printing. Thermal, electrochemical, and catalytic curing methods are also possible.

5) After curing, the probe head 208, which is connected to a potentiostat 209, is lowered to touch the electrical connections on the substrate 202. The deposition nozzle 206 is aligned such that it lowers into the dump region, or for example a hole in the board, to begin the transition to the next formulation and remove the unwanted formulation mix volume left within the deposition nozzle 206. With contact between the two point probe head 208 and the electrode connections on the substrate 202 (i.e., when the substrate 202 is an impedance characterization substrate), electrical impedance spectroscopy measurements are made traditionally from one or more selected frequencies, and in some embodiments frequencies of 7 MHz to 100 mHz and in some embodiments ranges of 35 MHz to 10 μHz are also possible. With the dimensions and probe locations on the present characterization substrate 202, over twelve measurements are possible for a single printed film by moving the probe head 208 around on the substrate 202 to varying electrode connections. Traditionally, 4-6 spatial measurements are done for each film. Measurements may be done in triplicate, and the average of all measurements for one film may be used and recorded in the database **218*a*1** for the sample for comparison.

In addition to impedance measurements, confocal machine vision techniques may also be used to measure the height of films as deposited on the substrate 202. These, in conjunction with images of the samples from above, and profilometry data (after deposition end), are used to train a machine learning model (e.g., one or more models of the machine learning software models **218*a*2**) to accurately measure the height of the sample. These height measurements are used to generate corrected ionic conductivity measurements for each sample from the raw impedance measurements.

The average data from a batch of runs is then inputted into the experimental planning software module **218*a*, which uses this data to identify regions of uncertainty and interest. These regions are used to generate the deposition file for next batch of formulations tested. For example, if 12 samples were printed and the impedance of each measured, it may be that a region of uncertainty or interest worthy of closer examination becomes apparent between the formulations used to print samples 3, 4 and 5. The experimental planning software module 218*a*** may then be used to calculate a new batch of formulations to more closely explore the regions between defined between the previously printed samples 3-5.

This process continues (steps 3-7) until the substrate 202 is filled with samples and deposition concludes. After testing, identified films with high ionic conductivities are characterized further electrochemically and thermomechanically. This data is also included in the database **218*a*1**.

In between testing, the models of the machine learning software module **218*a*2** are trained with all existing datasets and updated for the next round of testing.

The machine learning software module **218*a*2 includes, but is not limited to, small-data models like Gaussian Processes and Random Forest Ensembles, as well as large-data models including Neural Networks. Additionally, the machine learning software module 218*a*2 includes, but is not limited to, algorithms such as Bayesian optimization for modeling and decision-making. The exact machine learning model in use depends on the available data. These machine learning models are first trained with some initial test data, and then improved between tests when new materials are screened and the living materials database 218*a*1 grows. Specifically, during deposition and testing, some batches of data are produced at the beginning. The models of the machine learning software module 218*a*2 are trained using these initial batches of data and then used to help predict a new batch of formulations to print. A new batch of samples are printed for the predicted formulations and corresponding data is collected. This new batch of data is coupled to the previous batches to generate the following batch for further testing. In other words, all data generated during a test is used to make the new batch of testing, until testing is completed. Then this data is once again added to the database 218*a*1 and used to further improve the models within the machine learning software module 218*a*2 between tests. Critically, the machine learning software module 218*a*2** enables full automation of the materials formulation screening, and rapid homing in on desirable properties from the characterization and measurement data during testing.

Figure 2B:
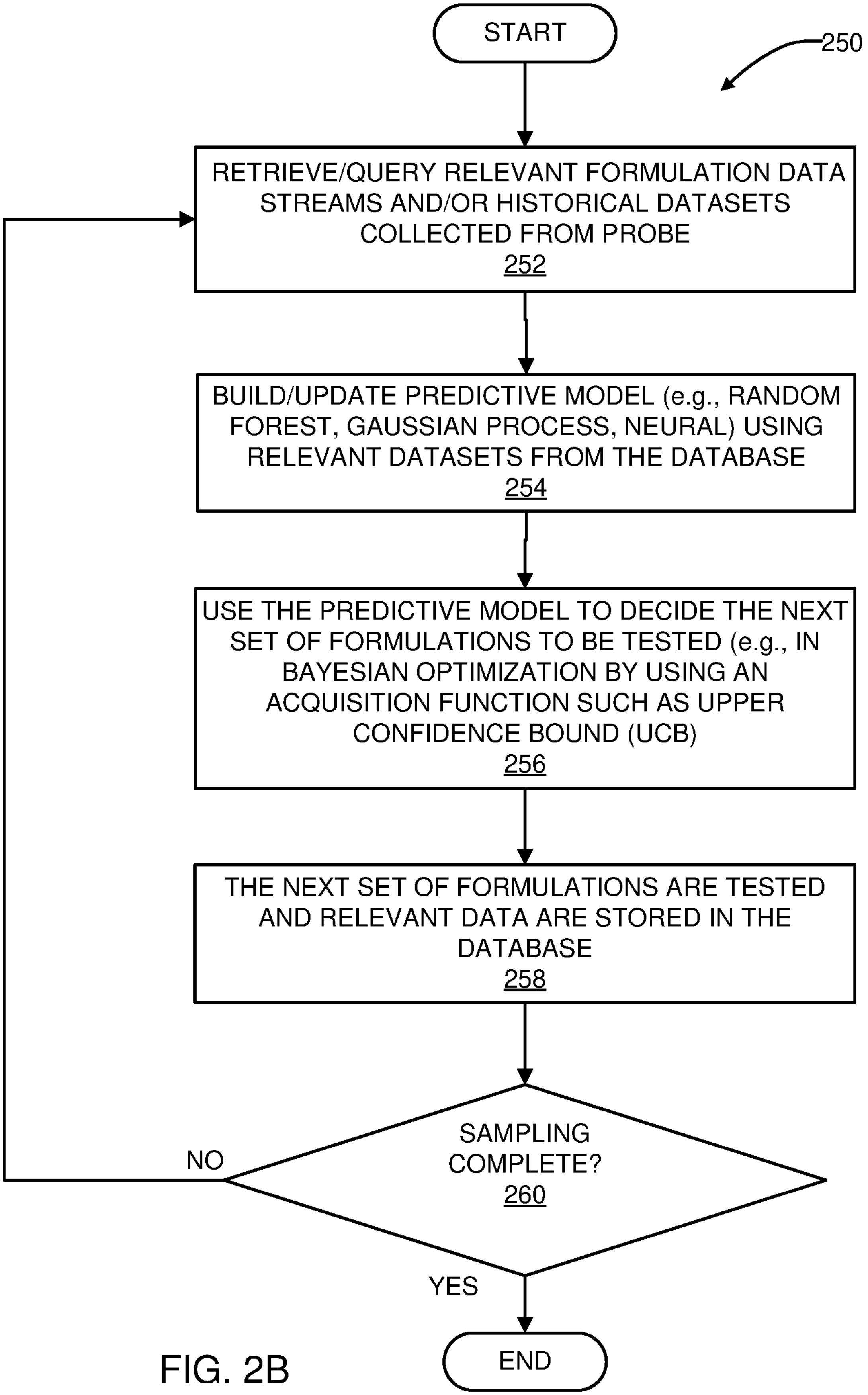
FIG. 2B is a high level flowchart of one example of operations that may be performed by the machine learning software module contained in the experimental planning software module.

Referring briefly to FIG. 2B, one example of operations performed by the machine learning software module **218*a*2 is shown in flowchart 250. In this example, an initial operation 252 is performed where the machine learning software module 218*a*2 retrieves/queries relevant formulation data streams and/or historical datasets collected from the probe 208. At operation 254 a predictive model is built/updated. The predictive model may be, without limitation, one or more Random Forest models, and/or one or more Gaussian Process models, and/or one or more Neural Network models. At operation 256 the predictive model is used to decide the next set of formulations to be tested. In one example this may be carrying out Bayesian optimization by using an acquisition function such as upper confidence bound (UCB). At operation 258 the next set of formulations are tested and relevant data are stored in the database. At operation 260 a check is made if sampling is complete, and if not, operations 252-256 may be repeated. If the check at operation 258** produces a "Yes" answer, then sampling is complete.

Automated High Throughput Polymer Electrolyte Screening

Figure 3:
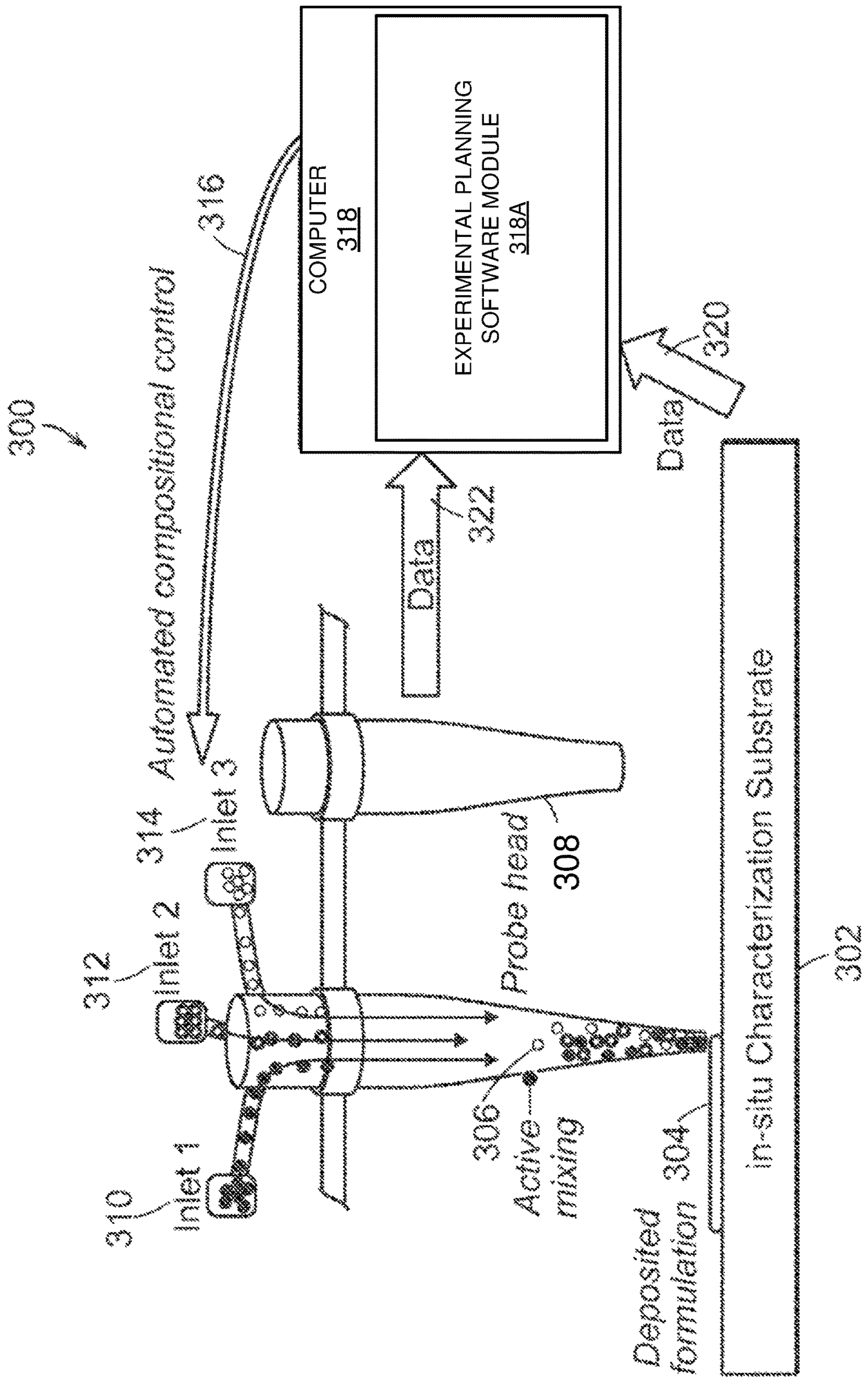
FIG. 3 is an illustration of automated high throughput polymer electrolyte screening.

Referring now to FIG. 3, an illustrative view shows an embodiment of Applicant's apparatus, systems, and methods. This embodiment is identified generally by the reference numeral 300. The components of Applicant's system 300 illustrated in FIG. 3 are listed below:

- Reference Numeral No. 302—In-situ Characterization Substrate,
- Reference Numeral No. 304—Deposited Formulation,
- Reference Numeral No. 306—Mixing and Deposit Head,
- Reference Numeral No. 308—Probe Head,
- Reference Numeral No. 310—Inlet 1,
- Reference Numeral No. 312—Inlet 2,
- Reference Numeral No. 314—Inlet 3,
- Reference Numeral No. 316—Automated Compositional Control,
- Reference Numeral No. 318—Computer with database and experimental planner,
- Reference Numeral No. 320—Data from Substrate, and
- Reference Numeral No. 322—Data from Probe Head.

It will be appreciated that the system 300 in this example also includes the syringes and associated motors described in connection with the system 200, and those components may be controlled just as described for the system 200. Likewise, the experimental planner software module **318*a* may be identical or similar in construction to the module 218, and may include components identical to the database 218*a*1, the machine learning models 218*a*2 and the new batch formulation generation software module 218*a*3**.

The description of the structural components of the Applicant's apparatus, systems, and methods 300 having been completed, the operation and additional description of the Applicant's apparatus, systems, and methods will now be considered in greater detail. Applicant's apparatus, systems, and methods 300 involve three main components: (1) Formulations loading and mixing, (2) Deposition and measurement, and (3) Analysis and experimental planning.

General Description of Operation of FIG. 3

Load test samples into inlets 310, 312, and 314.

Mix 306 and deposit 304 films in batches.

Data from Probe Head 322 and Data from Substrate 302 are sent to Computer 318 with database and the experimental planning software module 318*a*.

Measure characteristic of interest through contact between probe 308 and In-situ Characterization.

Record data of batch of test samples on computer 318.

Computer 318 takes data from previous batches to dictate next batch printed 316.

Repeat until done (when substrate is filled or no more space—Applicant contemplates up to 100 samples in a single screening).

More Detailed Description of Operation of FIG. 3

Prior to deposition, sample materials of interest are first loaded into the inlets 310, 312, and 314 of deposition nozzle 306. Note that FIG. 3 shows three inlets; however, more inlets are contemplated and only three are shown for illustrative purposes. Each of these inlets 310, 312 and 314 may receive samples. Examples of the samples include polymer electrolyte resin formulations including components such as solvents, monomers, oligomers, polymers, initiators and curing agents, salts, stabilizers, plasticizers, and solid additives such as silica, ceramics, nanoparticles, and metals. Once the inlets 310, 312, 314 are loaded and mixed within the deposition nozzle 306, deposited sample composition 304 is controlled through the apparatus 300, varying the ratio of material supplied into the inlets 310, 312 and 314 into the deposition nozzle 306. The ratios of the materials supplied to the inlets 310, 312 and 314 can be kept constant or varied throughout testing, producing deposited materials with homogeneous, heterogenous, and graded compositions. Mixing of the components within the deposition nozzle 306 can be achieved through static or active mixing techniques as described herein for the deposition nozzle 206. Active mixing techniques are illustrated in FIG. 3 and utilize a rotating mixing shaft within the mixing head to shear mix the inlet materials. Active mixing is generally chosen for polymer electrolytes, as homogenous mixing of formulations with viscosities ranging from liquids to gels and pastes is possible. The rotational rate of the mixing shaft, coupled with the feed rate of inlets, impacts the mixing time and turbidity within the system, and thereby the homogeneity of 304. The deposition nozzle 306 may include shear, pressure, and thermal inputs to enable deposition and analysis of the mixed resin formulations 304.

Mixed formulations are then deposited as samples 304 (e.g., films) onto a substrate 302. Deposited samples 304 can include liquids, gels pastes, and thermoplastics. With the inclusion of crosslinkers, the formulations can be cured using photo, thermal, chemical, or other curing mechanisms. For screening, the samples 304, if they have been deposited in the form of thin films, are generally targeted. In the case of system 300, polymer electrolyte measurements are focused on impedance characterization. With contact between the two point probe head 308 and the electrode connections on the substrate 302, electrical impedance spectroscopy measurements are made traditionally from frequencies of selected frequencies, in some embodiments frequencies of 7 MHz to 100 mHz. The use of frequency ranges of 35 MHz to 10 μHz are possible and anticipated. In some embodiments over twelve measurements may be made for a single film, moving the probe head 308 around on the substrate 302 to varying electrode connections and locations on the deposited material 304 spatially. Traditionally, 4-6 spatial measurements are done for each deposited material film. Measurements may be done in triplicate, and the average of all measurements for one film is used and recorded in the internal database of the experimental planning software module 318 for the sample for comparison. Additional probe heads and substrates contemplated in the system 300 include, optical metrology and imaging, stress sensing, chemical compositional analysis, fluorescence, pH, and environmental measurements (temperature, humidity). In addition, probe head 308 and substrates 302 can be utilized to align and interact with deposited materials. This includes electromagnetic alignment of particles, electrochemical and surface chemistry interactions, and photo or thermal curing and interactions. Probe head 308 and substrate 302 inputs and measurement 320 information are controlled and recorded as data within the computer 318 and its respective software 318*a*. This data is kept for each print and formulation tested.

The experimental planning software module 318*a* for this system 300 is used to control the feed ratios of the materials applied to the inlets 310, 312 and 314 during screening. Between tests, machine learning models that are used in the experimental planning software module 318*a* are improved through analysis of the full living database of previous test materials screened. Machine learning models include, but are not limited to Bayesian optimization, random forest, and Gaussian processes, as well as large data models including neural networks. During deposition and testing, the latest model is used to analyze the data from the initial batches of testing. From this data, a new batch of formulations to test is generated, and printing continues. This new batch data is coupled to the previous batches to generate the following batch for further screening. In other words, all data generated during a test is used to make the new batch of testing, until testing is completed. Then this data is once again added to the database within the experimental software planning software module 318*a* and used to improve the module 318*a*. Critically, the experimental planning software module 318*a* enables full automation of the materials formulation screening, and rapid homing in on desirable properties from the characterization and measurement data obtained during testing.

Example of Polymer Electrolyte Printing

Step 1—Material formulations are made using any combination of the following components: solvent, monomer, oligomer, polymer, crosslinkers, salts, photoinitiators, catalysts, stabilizers, dyes, liquid additives and solid additives. Viscosities from liquids to high viscosity gels and pastes are possible.

Step 2—Formulations are loading into inlet syringes, and motor ratios are used to control the varying composition. Two to four different syringe inlets for the deposition nozzle 306 are possible, with traditional testing using two syringes to vary a single variable. Example variables include salt concentration, additive concentration, and polymer additive concentration.

Step 3—Inlet materials are mixed in the mixing body and deposited onto the impedance characterization substrate 302. The rotational speed and pressure of the mixing element within the deposition nozzle 306 dictate turbidity, deposition rate, and homogeneity of the formulations. Samples are generally printed at a fixed syringe motor feed ratio (fixed composition), and then compositions of the materials may be switched between samples in a given test. 1-100 samples are possible in a single run with the substrate 302. Samples may also be graded or heterogeneous, switching ratios mid print. A dump region on the substrate 302 may be used to switch between different compositions between samples, as described herein before for the system 200.

Step 4—UV or blue light is traditionally used to cure the samples during printing. Thermal, electrochemical, and catalytic curing methods are also possible.

Step 5—After curing, the probe head 308 connected, may be connected to a potentiostat (such as potentiostat 209, but not shown in the Figure) is lowered to touch the electrical connections on the substrate 302. The deposition nozzle 306 is aligned such that it lowers into a dump zone, or a hole in the substrate 302, to begin the transition to the next formulation and remove the unwanted mix volume. With contact between the two point probe head 308 and the electrode connections on the substrate 302, electrical impedance spectroscopy measurements are made traditionally from selected frequencies, for example from 7 MHz to 100 mHz. Frequency ranges of 35 MHz to 10 μHz may also be used in some embodiments. Over twelve measurements are possible for a single film, moving the probe head 308 around on the substrate 302 to varying electrode connections. Traditionally, 4-6 spatial measurements are done for each film. Measurements may be done in triplicate, and the average of all measurements for one film may be used and recorded in the database of the experimental planning software module 318*a* for the sample for comparison.

Step 6—In addition to impedance measurements, confocal machine vision techniques are used to measure the height of films as deposited. These, in conjunction with images of the samples from above, and profilometry data (after deposition end), are used to train a machine learning model (identical or similar to the machine learning models 218*b*2) of the experimental planning software module 318 to accurately measure the height of the sample. These height measurements are used to generate corrected ionic conductivity measurements for each sample from the raw impedance measurements.

Step 7—The average data from a batch of runs is then inputted into the experimental planning software module 318*a*, which uses this data to identify regions of uncertainty and interest. These regions are used to generate the deposition file for next batch of formulations tested.

Step 8—This process continues (steps 3-7) until the substrate 302 is filled with samples and deposition concludes. After testing, identified films with high ionic conductivities are characterized further electrochemically and thermomechanically. This data is also included in the database.

Step 9—In between testing, the machine learning models within the experimental planning software module 318*a* are trained with all existing datasets and updated for the next round of testing.

The experimental planning software module 318*a* of the system 300 that controls the inlet feed ratios during screening may be implemented with machine learning models as described above and as described for the system 200. The machine learning models include, but are not limited to small-data models like Gaussian Processes and Random Forest Ensembles, as well as large-data models like feed-forward Neural Networks. The exact machine learning model in use depends on the available data. These machine learning models are first trained with some initial test data, and then improved between tests when new materials are screened and the living materials database within the experimental software module 318*a* grows. Specifically, during deposition and testing, some batches of data is produced at the beginning. Machine learning models are trained using these initial batches of data and predicts a new batch of formulations to print. A new batch of samples are printed for the predicted formulations and corresponding data is collected. This new batch of data is coupled to the previous batches to create the following batch. In other words, all data generated during a test is used to make the new batch of testing, until testing is completed. Then this data is once again added to the database of the experimental planning software module 318*a* and used to improve the next round of material formulation. Critically, this experimental software module 318*a* enables full automation of the materials formulation screening, and rapid homing in on desirable properties from the characterization and measurement data during testing.

Tuning Mechanical Strength 3D Printed Materials Screening

Figure 4:
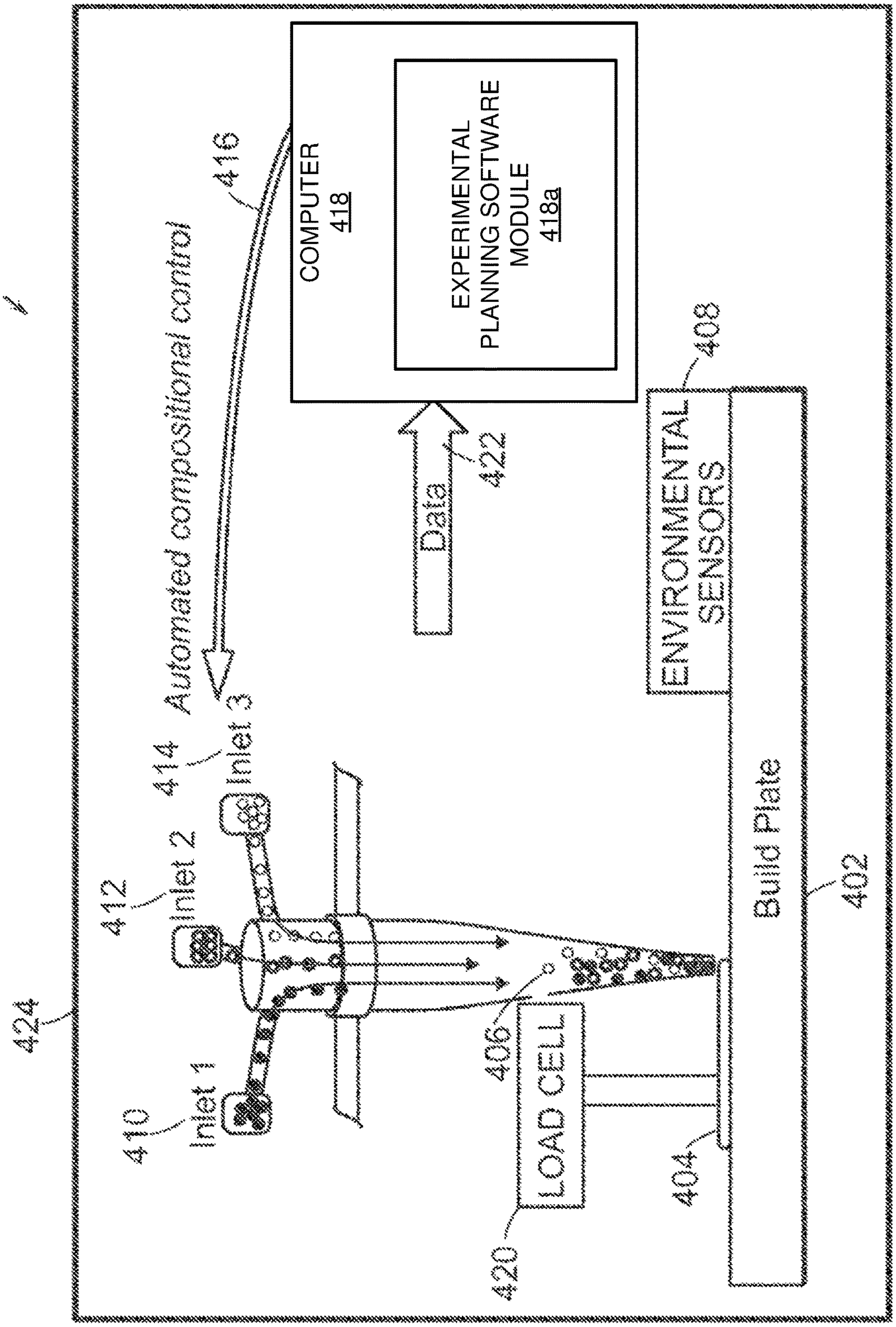
FIG. 4 is an illustration of tuning mechanical strength 3D printed materials screening.

Referring now to FIG. 4, an illustrative view shows yet another embodiment of Applicant's apparatus, systems, and methods. This system is identified generally by the reference numeral 400. The components of Applicant's system 400 as illustrated in FIG. 4 are listed below:

Reference Numeral No. 402—Build Plate,
Reference Numeral No. 404—Deposited Formulation,
Reference Numeral No. 406—Mixing and Deposition Head,
Reference Numeral No. 408—Environmental Sensors,
Reference Numeral No. 410—Inlet 1,
Reference Numeral No. 412—Inlet 2,
Reference Numeral No. 414—Inlet 3,
Reference Numeral No. 416—Automated Compositional Control,
Reference Numeral No. 418—Computer,
Reference Numeral No. 418*a*—Experimental Planning Software Module 418*a,*
Reference Numeral No. 420—Load Cell, and
Reference Numeral No. 422—Data from Probe Head and Load Cell and Environmental Sensors.
Reference Numeral No. 424—Controlled environment The description of the structural components of the Applicant's system 400 having been completed, the operation and additional description of the Applicant's system 400 will now be considered in greater detail.

General Description of Operation of the System 400 of FIG. 4

Applicant's system 400 provides tuning mechanical strength 3D printed materials screening.

Test sample formulations are loaded into inlets 410, 412, and 414. The deposited sample 404 can be test films or 3D samples.

The test sample 404 formulations are mixed in the deposition nozzle 406 and the test samples 404 are deposited on the build plate 402 providing test films or samples in batches. Deposited samples 404 may be standalone materials, or may be cured during or after deposition through stimulus such as, but not limited to, electromagnetic irradiation, acoustic wave, electric current, heat, and chemical crosslinking or interactions. Traditionally, light or heat are used to cure the deposited samples.

Information about the test films or samples 404 in batches on the build plate 402 is obtained from the load cell 420 and environmental sensors 408 and data 422 is provided to the computer 418 with its database and its experimental planning software module 418*a*. Environmental sensors can be used in tandem with controlled environments 424 such as oven heating, electromagnetic irradiation, humidifier, and non-ambient gas flow environments.

The automated software in the computer 418, which may be same or similar to the components described with the system 200, takes data obtained from previous batches to dictate next batch printed 416.

The above steps are repeated until done (when the substrate or build plate 402 is filled or no more space available—Applicant contemplates up to 100 samples in a single screening).

More Detailed Description of Operation of the System 400 of FIG. 4

Prior to deposition, sample materials of interest are first loaded into the inlets 410, 412, and 414. Note that FIG. 4 shows three inlets; however, more inlets are contemplated and only three are shown for illustrative purposes. Each of these inlets 410, 412, 414 will include samples. Once the inlets 410, 412, 414 are loaded, and mixed to the desired formulation, the test samples will be deposited on the build plate 404 providing test films or samples in batches. The deposited sample composition 404 is controlled through the system 400, varying the ratio of materials supplied to the inlets 410, 412, 414 of the deposition nozzle 406. The ratios of materials supplied can be kept constant or varied throughout testing, producing deposited materials with homogeneous, heterogenous, and graded compositions.

Mixing of the components within the deposition nozzle 406 can be achieved through static or active mixing techniques as described hereinbefore for the system 200. The deposition nozzle 406 may include shear, pressure, and thermal inputs to enable deposition and analysis of the mixed resin formulations 404.

Mixed formulations 404 are deposited onto the build plate 402. Deposited sample formulations 404 can include liquids, gels, pastes, and thermoplastics. Probe head 406 and build plate 402 inputs, controlled environment inputs 424, and measurements from the load cell 420 and the probe head 408 are controlled and recorded as data 422 within the computer 418 and its respective experimental planning software module 418*a*. This data is kept for each print and formulation tested. Applicant's system 400 and related and methods provide screening of the tuned mechanical strength of 3D printed materials to determine parameters for targeted applications.

The experimental planning software module for the system 400 is used to control the inlet feed ratios during screening. Between tests, machine learning models that are used in the apparatus's 400 experimental planning software module are improved through analysis of the full living database of previous test materials screened, as explained herein for the module 218*a*. Machine learning models include, but are not limited to Bayesian optimization, random forest, and Gaussian processes, as well as large data models including neural networks. During deposition and testing, the latest model is used to analyze the data from the first batch of testing. From this data, a new batch of formulations to test is generated, and printing continues. This new batch data is analyzed relative to the previous batches to generate the following new batch of formulations for further testing. In other words, all data generated during a test is used to make the new batch of testing, until testing is completed. Then this data is once again added to the database of the experimental planning software module 418*a* and used to improve the experimental planner. Critically, this planner enables full automation of the materials formulation screening, homing in on desirable properties from the characterization and measurement data during testing.

Tuning Mechanical Strength 3D Printed Materials Screening

Figure 5:
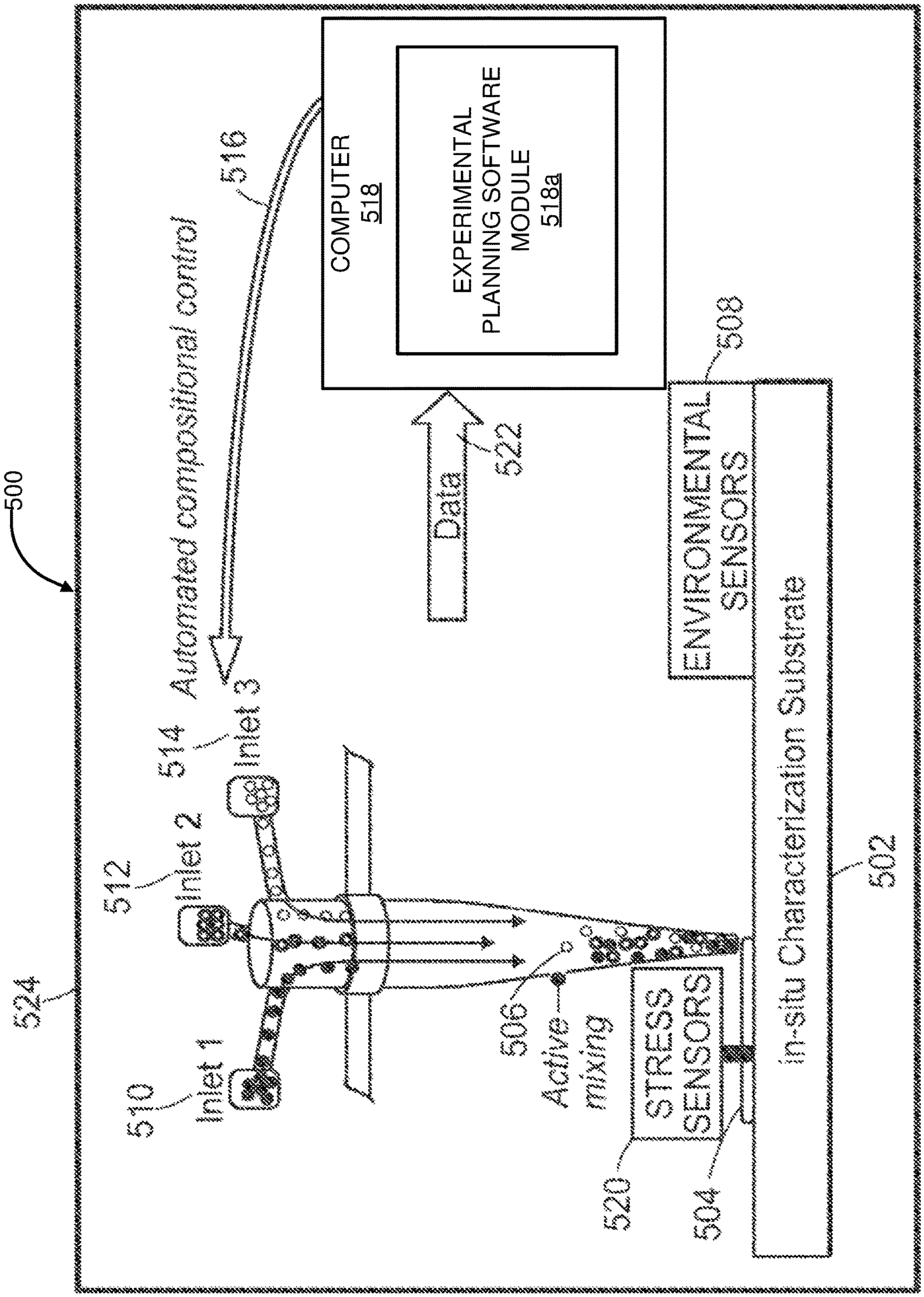
FIG. 5 is an illustration of tuning mechanical strength and other thermomechanical properties for 3D printed materials screening.

Referring now to FIG. 5, an illustrative view shows yet another embodiment of Applicant's apparatus, systems, and methods. The system of this embodiment is identified generally by the reference numeral 500. The components of the system 500 illustrated in FIG. 5 are listed below:

The components of Applicant's system 500 illustrated in FIG. 5 are listed below:

Reference Numeral No. 502—Build Plate,
Reference Numeral No. 504—Deposited Formulation,
Reference Numeral No. 506—Mixing and Deposit Head,
Reference Numeral No. 508—Environmental Sensors,
Reference Numeral No. 510—Inlet 1,
Reference Numeral No. 512—Inlet 2,
Reference Numeral No. 514—Inlet 3,
Reference Numeral No. 516—Automated Compositional Control,
Reference Numeral No. 518—Computer,
Reference Numeral No. 518*a* Experimental Planning Software Module 518*a*,
Reference Numeral No. 520—Stress Sensors, and
Reference Numeral No. 522—Data from Probe Head and Stress Sensors and Environmental Sensors.
Reference Numeral No. 524—Controlled environment The description of the structural components of the Applicant's apparatus, systems, and methods 500 having been completed, the operation and additional description of the Applicant's apparatus, systems, and methods will now be considered in greater detail.

General Description of Operation of the system 500 of FIG. 5

Applicant's system 500 and its related methods of operation provide tuning mechanical strength and other thermomechanical properties for 3D printed materials screening.

Test sample formulations are loaded into inlets 510, 512, and 514 of the deposition nozzle 506. The deposited sample 504 can be test films or 3D samples.

The test sample 504 formulations are mixed in the deposition nozzle 506 and then deposited on the build plate 504 providing test films or samples 504 in batches. Deposited samples 504 may be standalone materials, or may be cured during or after deposition through stimulus such as electromagnetic irradiation, acoustic wave, electric current, heat, and chemical crosslinking or interactions. Traditionally, light or heat are used to cure the deposited samples.

Information about the test films or samples 504 in batches on the build plate 504 is obtained from the Stress Sensors 520 and environmental sensors 508 and data 522 is provided to the computer 518 with its experimental planning software module 518 and internal database (similar or identical to the module 218*a*). The environmental sensors 508 can be used in tandem with one or more controlled environments 524 such as oven heating, electromagnetic irradiation, humidifier, and non-ambient gas flow environments.

The automated experimental planning software module 518*a* in the computer 518 with its database (e.g., the same or similar to the database 218*a*1) takes data obtained from previous sample 504 batches to analyzes the data to calculate formulations to be used for the next batch of materials 516 to be printed.

The above steps are repeated until done (when substrate is filled or no more space—Applicant contemplates up to 100 samples in a single screening).

More Detailed Description of Operation of the System 500 of FIG. 5

Prior to deposition, sample materials of interest are first loaded into the inlets 510, 512, and 514. Note that FIG. 5 shows three inlets being used with the deposition nozzle 506; however, more inlets are contemplated and only three are shown for illustrative purposes. Each of these inlets 510, 512 and 514 will be fed with samples from separate associated syringes (not shown but similar or identical to syringes 210, 212 and 214 of system 200). Once the inlets 510, 512, 514 are loaded, and mixed within the deposition nozzle 506 to the desired formulation, the test samples will be deposited on the build plate 504 providing test films or samples 504 in batches. The deposited sample composition 504 is controlled through the system 500, varying the ratio of materials supplied between the inlets 510, 512 and 514 into the deposition nozzle 506. The ratios of the materials supplied can be kept constant or varied throughout testing, producing deposited materials with homogeneous, heterogenous, and graded compositions.

Mixing of the components within the deposition nozzle 506 can be achieved through static or active mixing techniques as described hereinbefore. The deposition nozzle 506 may include shear, pressure, and thermal inputs to enable deposition and analysis of the mixed resin formulations 504.

Mixed formulations are deposited as samples 504 onto the build plate 502. Deposited samples 504 can include liquids, gels, pastes, and thermoplastics. Deposited samples 504 may be standalone materials, or may be cured during or after deposition through stimulus such as electromagnetic irradiation, acoustic wave, electric current, heat, and chemical crosslinking or interactions. Traditionally, light or heat are used to cure the deposited samples 504. Probe head 506 and build plate 502 inputs, controlled environment inputs 524, and measurements from stress sensors 520 and environmental sensors 508 are controlled and recorded as data 522 within the computer 518 and its respective experimental planning software module 518. This data is kept for each print and formulation tested. Applicant's system 500 and related methods provide screening of the tuned mechanical strength and other thermomechanical properties of 3D printed materials to determine parameters for targeted applications.

The experimental planning software module 500 for the system 500 is used to control the feed ratios of the materials supplied to the inlets 510, 512 and 514 during screening and is implemented through machine learning models of the experimental planning software module 518*a*. Machine learning models may include, but are not limited to, Bayesian optimization, random forest, and Gaussian processes, as well as large data models like feed-forward neural networks. During deposition and testing, the latest model is used to analyze the data from the first batch of testing. From this data, a new batch of formulations to test is generated, and printing continues. This new batch data is coupled to the previous batches to generate the following batch for further screening. In other words. all data generated during a test is used to make the new batch of testing, until testing is completed. Then this data is once again added to the database and used to improve the experimental planning software module 518 and its machine learning models. Critically, experimental software planning module 518*a* enables full automation of the materials formulation screening, homing in on desirable properties from the characterization and measurement data during testing.

Long-term cell culture study

Figure 6:
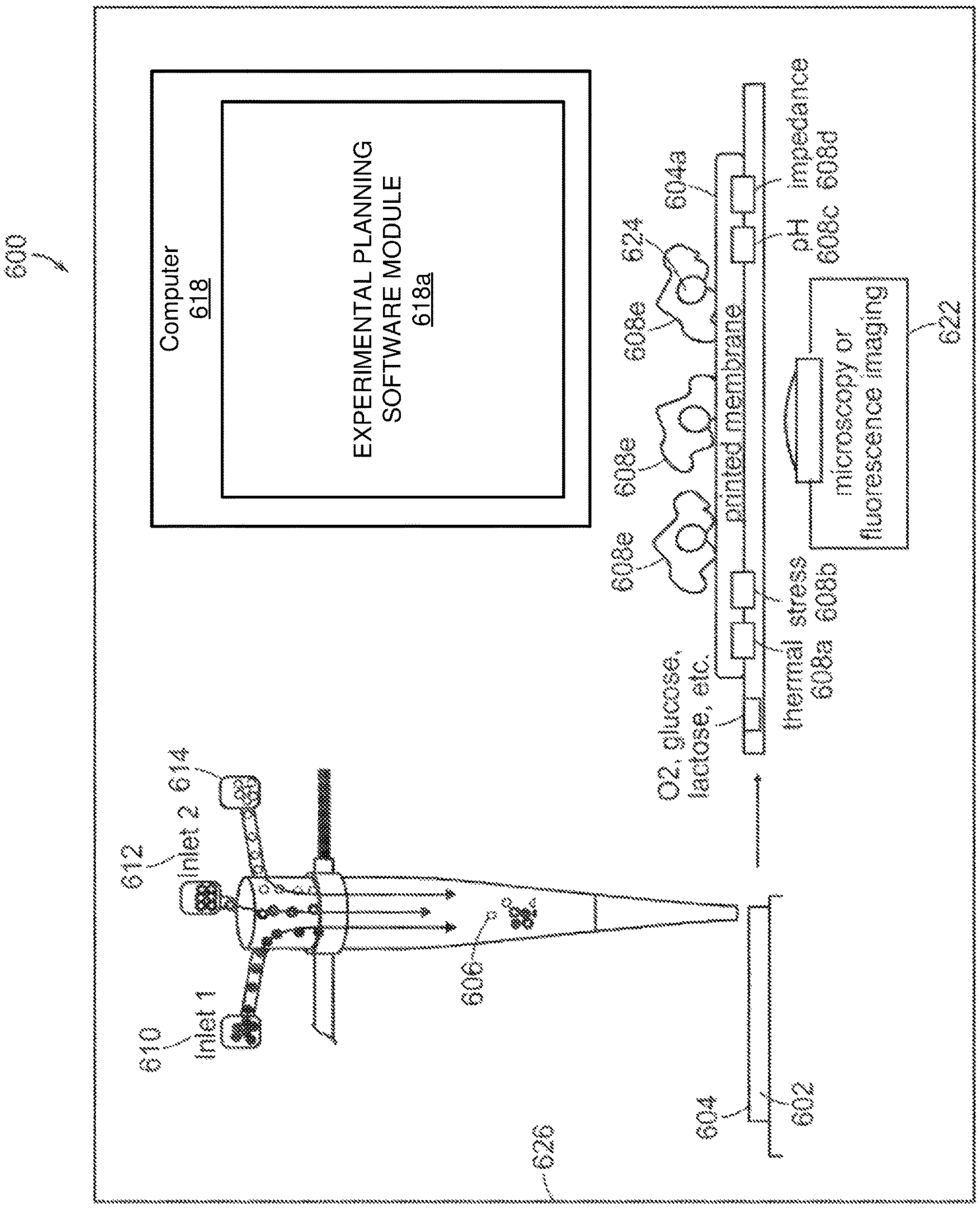
FIG. 6 is an illustration of a screening system for screening a material.

Referring now to FIG. 6, an illustrative view shows another embodiment of Applicant's apparatus, systems, and methods. This system of this embodiment is identified generally by the reference numeral 600. The components of Applicant's 600 as illustrated in FIG. 6 are listed below:

Reference Numeral No. 602—Build Plate,
Reference Numeral No. 604—Deposited Formulation,
Reference Numeral No. 606—Mixing and Deposit Head,
Reference Numeral No. 608*a*—Thermal Sensors,
Reference Numeral No. 608*b*—Stress Sensors,
Reference Numeral No. 608*c*—pH Sensors,
Reference Numeral No. 608*d*—Impedance Sensors,
Reference Numeral No. 608*e*—O2, Glucose, Lactate Sensors,
Reference Numeral No. 610—Inlet 1,
Reference Numeral No. 612—Inlet 2,
Reference Numeral No. 614—Inlet 3,
Reference Numeral No. 618—Computer,
Reference Numeral No. 618*a*—Experimental Planning Software Module,
Reference Numeral No. 622—Microscopy or Fluorescence Imaging Subsystem,
Reference Numeral No. 624—Cells
Reference Numeral No. 626—Environmental chamber The description of the structural components of the Applicant's system 600 having been completed, the operation and additional description of the Applicant's system and its related methods of operation will now be considered in greater detail.

Applicant's system 600 provides materials screening.

Test sample formulations are loaded into inlets 610, 612, and 614 of the deposition nozzle 606. The deposited sample 604 can be test films or 3D samples.

The test sample formulations are mixed in the deposition nozzle 606 and the test samples 604 are deposited on the build plate 602 providing test films or samples in batches. Cells 624 can be seeded directly into the test sample 604 formulations or cultured onto the deposited films forming the samples 604 after printing. After printing, build plate 602 with samples is transferred to an environmental chamber 626 for continued study. Optionally, a microscopy or fluorescence imaging subsystem 622 may be disposed adjacent the build plate 602 and used to image a portion test samples to assist in the analysis of the test samples.

Information about the test films or samples 604 in batches on the build plate 602 and information from the cells 624 are obtained using the Thermal Sensors 608*a*, Stress Sensors 608*b*, pH Sensors 608*c*, Impedance Sensors 608*d*, and/or 02, Glucose, Lactate Sensors 608*e*, and data is provided to the computer 618 with its experimental planning software module 618*a* and the internal database thereof (where the experimental planning software module 618 may by identical or similar in construction to the module 218*a*). In addition to measurements taken directly at printing, these sensors can be utilized to monitor samples and cell culture over time. The computer 618 with the experimental planning software module 618*a* and its internal database takes data obtained from previous batches to dictate next batch printed. Multiple build plates 602 can be loaded into the environmental chamber 626 at the same time, providing continued study of multiple screenings over prolonged periods of study.

The above steps are repeated until done (when substrate is filled or no more space—Applicant contemplates up to 100 samples in a single screening, multiple screenings per environmental chamber).

Environmental, Permeability, and Sample Aging Studies

Figure 7A:
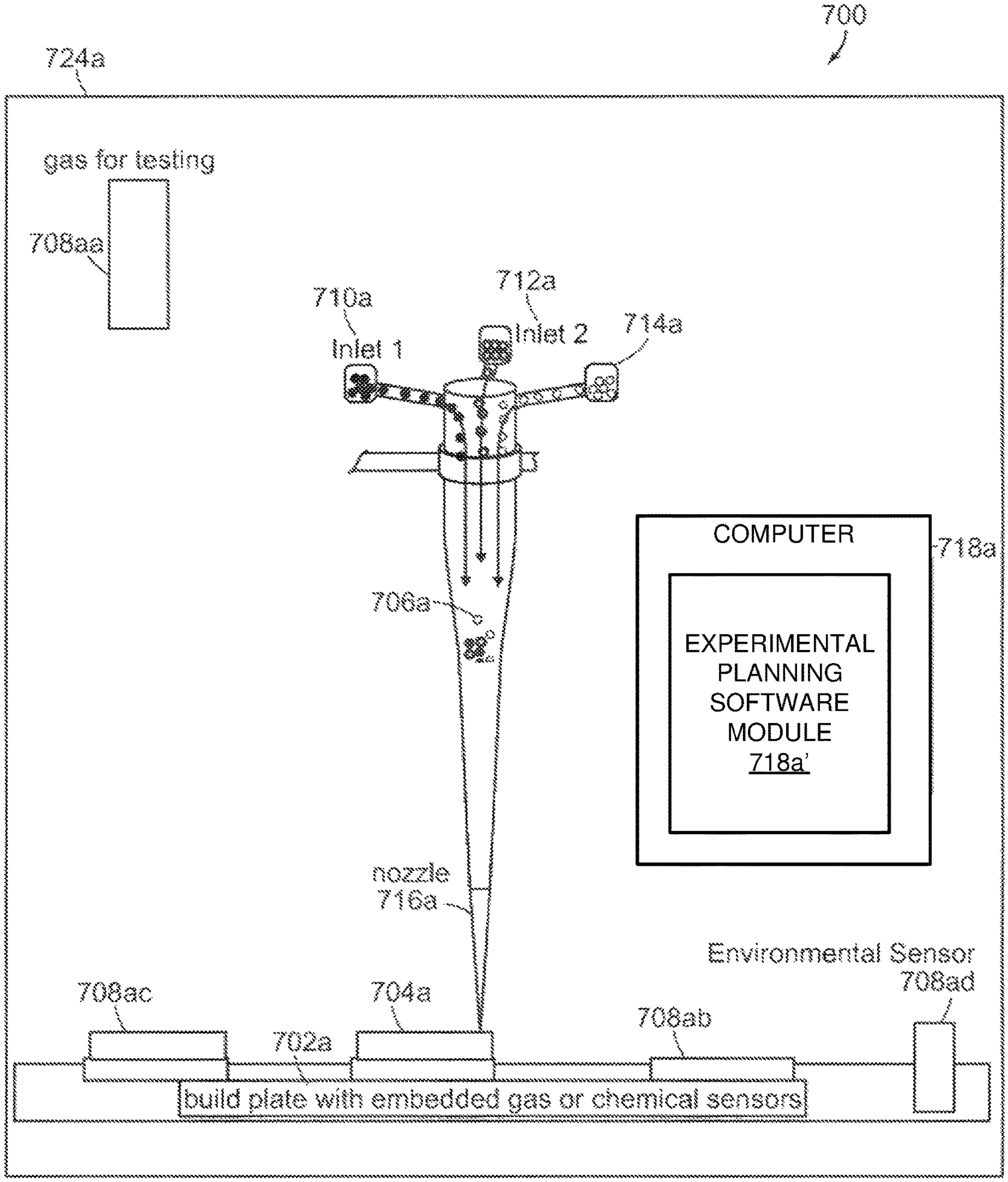
FIG. 7A is an illustration of another embodiment of a screening system for screening a material.

Referring now to FIG. 7A, an illustrative view shows another embodiment of Applicant's apparatus, systems, and methods. This system of this embodiment is identified generally by the reference numeral 700*a*. The components of Applicant's system 700*a* as illustrated in FIG. 7A are listed below:

The components of Applicant's system 700*a* and its related methods of operation are listed below:

Reference Numeral No. 702*a*—Build Plate,

Reference Numeral No. 704*a*—Deposited Formulation,

Reference Numeral No. 706*a*—Mixing and Deposition Head,

Reference Numeral No. 708*aa*—Gas for Testing,

Reference Numeral No. 708*ab*—Sensors for Gas or Chemical,

Reference Numeral No. 708*ac*—Additional Sensors for Testing or Stimulus for Aging Study, Reference Numeral No. 708*ad*—Environmental Sensors, Reference Numeral No. 710*a*—Inlet 1, Reference Numeral No. 712*a*—Inlet 2, Reference Numeral No. 714*a*—Inlet 3, Reference Numeral No. 716*a*—Deposition Nozzle, Reference Numeral No. 718*a*—Computer, Reference Numeral No. 718 a'—Experimental Planning Software Module;

Reference Numeral No. 724*a*—Controlled environment

The description of the structural components of the Applicant's system 700*a* having been completed, the operation and additional description of the Applicant's system and its methods of operation will now be considered in greater detail.

Applicant's system 700*a* provides materials screening.

Test sample formulations are loaded into inlets 710*a*, 712*a*, and 714*a* of the deposition nozzle 716. The deposited sample 704*a* can be test films or 3D samples.

The test sample formulations are mixed in the deposition nozzle 716*a* and the test samples are deposited on the build plate 702*a* providing test films or samples in batches. Deposited samples may be standalone materials, or may be cured during or after deposition through stimulus such as electromagnetic irradiation, acoustic wave, electric current, heat, and chemical crosslinking or interactions. Traditionally, light or heat are used to cure the deposited samples.

Information about the test films or samples in batches on the build plate 702*a* is obtained in relation to responses to Gas, Chemicals, Stimulus, etc. 708*aa*. This includes gas and chemical permeability studies, aging studies, and stimuli-responsive material studies, for example. Sample responses are measured through embedded gas and chemical sensors 708*ab* in the build plate 702*a*. In addition, other embedded or drop-down sensors and stimuli may be incorporated for further testing, such as stress and thermal sensors, impedance sensors or electrode arrays, and imaging. With a controlled environment 724*a*, measurements can be made at initial printing, as well as over time through continued study. The controlled environment 724*a* can be envisioned as being present both around the deposition system 700*a*, as well as an external chamber for continued study after deposition. The use of an external chamber would also enable continued study of multiple screenings at the same time.

The automated experimental planning software module 718*a*' in the computer 718, with its internal database, takes data obtained from previous batches to determine the formulations for the next batch of samples to be printed.

The above steps are repeated until done (when substrate is filled or no more space—Applicant contemplates up to 100 samples in a single screening, multiple screenings studied over time simultaneously).

Figure 7B:
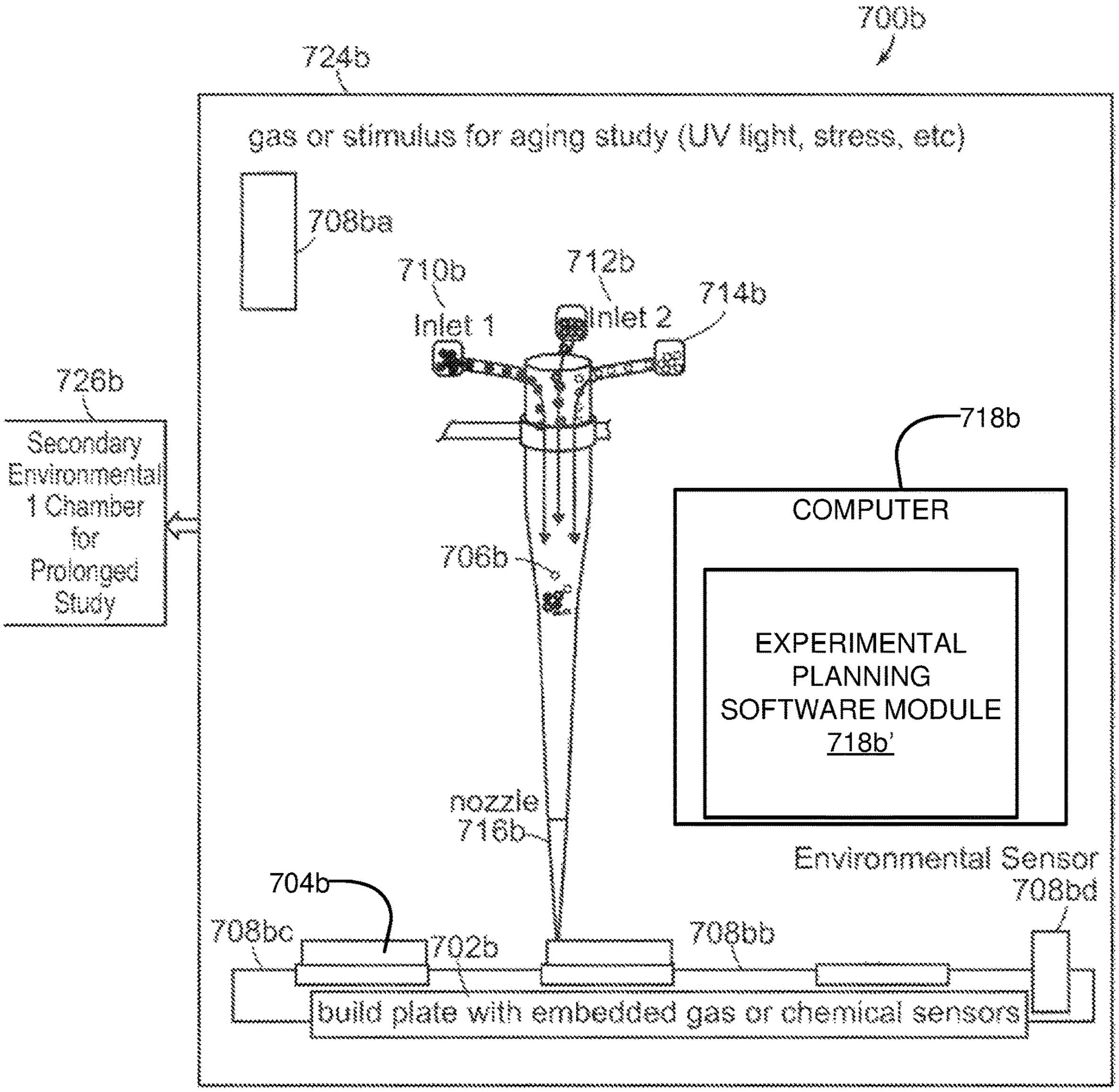
FIG. 7B is an illustration of yet another embodiment of a screening system for screening a material.

Referring now to FIG. 7B, an illustrative view shows another embodiment of Applicant's apparatus, systems, and methods. The system of this embodiment is identified generally by the reference numeral 700*b*. The components of Applicant's system 700*b* are listed below:

Reference Numeral No. 702*b*—Build Plate,

Reference Numeral No. 704*b*—Deposited Formulation,

Reference Numeral No. 706*b*—Mixing and Deposition Head,

Reference Numeral No. 708*ba*—Gas or Stimulus for Curing, and/or Gas or Stimulus for Aging Study (UV light, stress, etc.), Reference Numeral No. 708*bb*—Sensors for Gas or Chemical, Reference Numeral No. 708*bc*—Additional Sensors for Testing or Stimulus for Aging Study, Reference Numeral No. 708*bd*—Environmental Sensors, Reference Numeral No. 710*b*—Inlet 1, Reference Numeral No. 712*b*—Inlet 2, Reference Numeral No. 714*b*—Inlet 3, Reference Numeral No. 716*b*—Deposition Nozzle, Reference Numeral No. 718*b*—Computer, Reference Numeral No. 718*b*'—Experimental Planning Software Module Reference Numeral No. 724*b*—Controlled environment, and Reference Numeral No. 724*b*—Secondary chamber for prolonged study.

Reference Numeral 726*b*—Secondary environmental chamber for continued study.

The description of the structural components of the Applicant's system 700*b* having been completed, the operation and additional description of the system will now be considered in greater detail.

Applicant's system 700*b* provides materials screening.

Test sample formulations are loaded into inlets 710*b*, 712*b*, and 714*b* of the deposition head 706*b*. The deposited sample 704*b* can be test films or 3D samples.

The test sample formulations are mixed in the nozzle and deposition head 706*b* and the test samples are deposited on the build plate 702*b* providing test films or samples 704*b* in batches. Deposited samples 704*b* may be standalone materials, or may be cured during or after deposition through stimulus such as electromagnetic irradiation, acoustic wave, electric current, heat, and chemical crosslinking or interactions 708*ba*. Traditionally, light or heat are used to cure the deposited samples.

Information about the test films or samples 704*b* in batches on the build plate 702*b* is obtained in relation to responses to Gas, Chemicals, Stimulus, or Gas for Age Study Testing or Stimulus for Aging Study (UV light, humidity, stress, heat, etc,) 708*ba*. This includes gas and chemical permeability studies, aging studies, and stimuli-responsive material studies, for example. Sample responses are measured through embedded gas and chemical sensors 708*bb*. In addition, other embedded or drop-down sensors and stimuli may be incorporated for further testing 708*bc*, such as stress and thermal sensors, impedance sensors or electrode arrays, and imaging. With a controlled environment 724*b*, measurements can be made at initial printing, as well as over time through continued study. Controlled environment 724*b* can be envisioned as being present both around the deposition system 700*b*, as well as an external chamber for continued study after deposition. The external chamber also enables continued study of multiple screenings at the same time. The secondary environmental chamber 726*b* may be in communication with the controlled environment 724*b* and may be used for further prolonged study of a component present in the controlled environment 724*b*.

The automated experimental planning software module 718*b*' (similar or identical to the module 218*a* of system 200) within the computer 718*b*, with its internal database, takes data obtained from previous batches to determine the formulations for the next batch of samples to be printed.

The above steps are repeated until done (when the substrate 702*b* is filled or no more space—Applicant contemplates up to 100 samples in a single screening, multiple screenings studied over time simultaneously). A Secondary chamber 724*b* is provided for prolonged study.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The claims are:

What is claimed is:

1. A system for screening a formulation of a material being printed in an additive manufacturing process, in situ, to enable rapid analysis, modeling and modification of at least one characteristic associated with the material formulation, the system comprising:

a computer;

a substrate on which the material formulation is printed;

a deposition print head for depositing the material formulation on the substrate as at least one material sample;

the substrate including a plurality of spatially separated electrodes which enable the characteristic of the material formulation printed thereon to be at least one of measured or determined;

a probe configured to be moved into contact with the material formulation after the material formulation is printed on the substrate as a sample material, the probe providing an output to the computer representing data from which the characteristic can be evaluated by the computer and a new material formulation determined;

the spatially separated electrodes being used to complete electrical paths as the probe contacts different areas of the material sample after the material formulation is printed on the substrate to form the material sample, to thus assist the probe in generating the data which is output to the computer; and an experimental planning software module including a machine learning software module, configured to use the data collected by the probe and to determine, using the machine learning software module, a new material formulation which better optimizes the characteristic being evaluated.

2. The system of claim 1, wherein the deposition print head includes at least first and second input ports for receiving first and second components of the material formulation being supplied to the deposition print head.

3. The system of claim 2, further comprising:

at least first and second syringes for containing the first and second components, respectively, of the material formulation; and first and second motors associated with the first and second syringes, respectively, and responsive to control signals from the computer, for controllably providing the first and second components to the deposition print head in accordance with the control signals from the computer.

4. The system of claim 3, wherein the computer generates the control signals in real time, and in situ, at least one of while or before the material sample is being printed.

5. The system of claim 1, wherein the experimental planning software module further includes:

a database for storing information and/or data associated with previously screened test materials, the database configured to be updated in real time with new material screening results provided by the probe output and updated formulation suggestions by the machine learning software module; and a new batch formulation software module for receiving information from the database and generating new formulations for a new batch of material samples to be printed.

6. The system of claim 1, wherein the machine learning software module comprises at least one of:

a random forest model;

a gaussian process model; or a neutral network model.

7. The system of claim 1, wherein the machine learning module comprises a Bayesian optimization framework for carrying out Bayesian modeling and decision making.

8. The system of claim 1, wherein the probe comprises a two point probe head including a first component which makes contact with the material sample, and a second component which extends through the material sample and into contact with at least one of the electrodes.

9. The system of claim 1, wherein the substrate further comprises an environmental sensor used to help provide additional data relating to the material sample to the computer.

10. The system of claim 1, wherein the substrate further comprises stress sensors used to help provide additional data relating to the material sample to the computer.

11. The system of claim 1, wherein the substrate comprises an impedance sensor used to help provide additional data relating to the material sample to the computer.

12. The system of claim 1, wherein the substrate comprises at least one of:

an O2 sensor;

a thermal sensor;

a pH sensor.

13. The system of claim 1, further comprising cells that are included in the material formulation when the material sample is printed on the substrate by the deposition print head, the cells further providing information enabling the characteristic to be evaluated.

14. The system of claim 1, further comprising a microscopy or fluorescence imaging subsystem for assisting in evaluating the material sample.

15. The system of claim 1, wherein the substrate forms a build plate having at least one of an embedded gas or a chemical sensor for generating information to assist the computer in evaluating the material sample printed on the build plate.

16. The system of claim 1, wherein:

the substrate and deposition print head are located inside a controlled environment.

17. The system of claim 16, wherein the controlled environment includes a stimulus to assist in evaluation of the material sample.

18. The system of claim 17, further comprising a secondary environmental chamber in communication with the controlled environment to enable further study of a component present in the controlled environment.

19. A method for screening a formulation of a material being printed in an additive manufacturing process, in situ, to enable rapid analysis, modeling and modification of at least one characteristic associated with the material formulation, the method comprising:

printing the material formulation as at least one material sample on a substrate, wherein the substrate is configured to have a plurality of spatially separated electrodes;

using at least one component associated with the substrate for enabling the characteristic of the material formulation printed thereon to be at least one of measured or determined;

using a probe to obtain information concerning the characteristic from the material sample;

wherein using the probe includes using the grid of spatially separated electrodes to complete electrical paths as the probe contacts different areas of the material sample after the material formulation is printed on the substrate to form the material sample, to thus assist the probe in generating the data which is output to the computer;

causing the probe to provide an output to a computer; and causing the computer to use software to evaluate the material sample, and wherein the software includes machine learning software to evaluate historical data concerning previously printed material samples, and to assist in determining updated formulations for new material samples to be printed on the substrate in subsequent printing operations and further analyzed.

* * * * *